US008383129B2

(12) United States Patent
Gonzalez-Mariscal et al.

(10) Patent No.: US 8,383,129 B2
(45) Date of Patent: Feb. 26, 2013

(54) **EMPLOYMENT OF ROTAVIRUS PROTEINS, DERIVED PROTEINS AND P

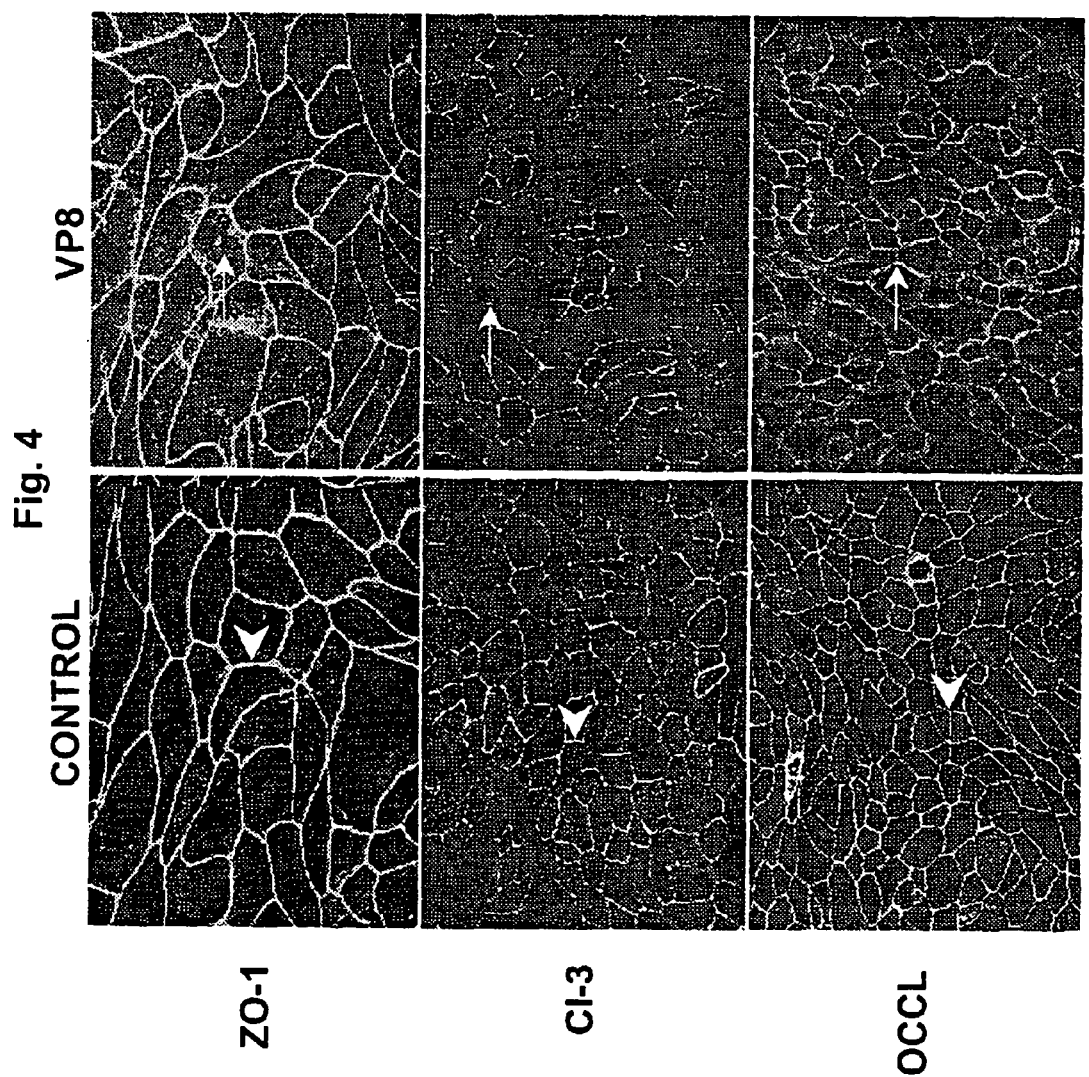

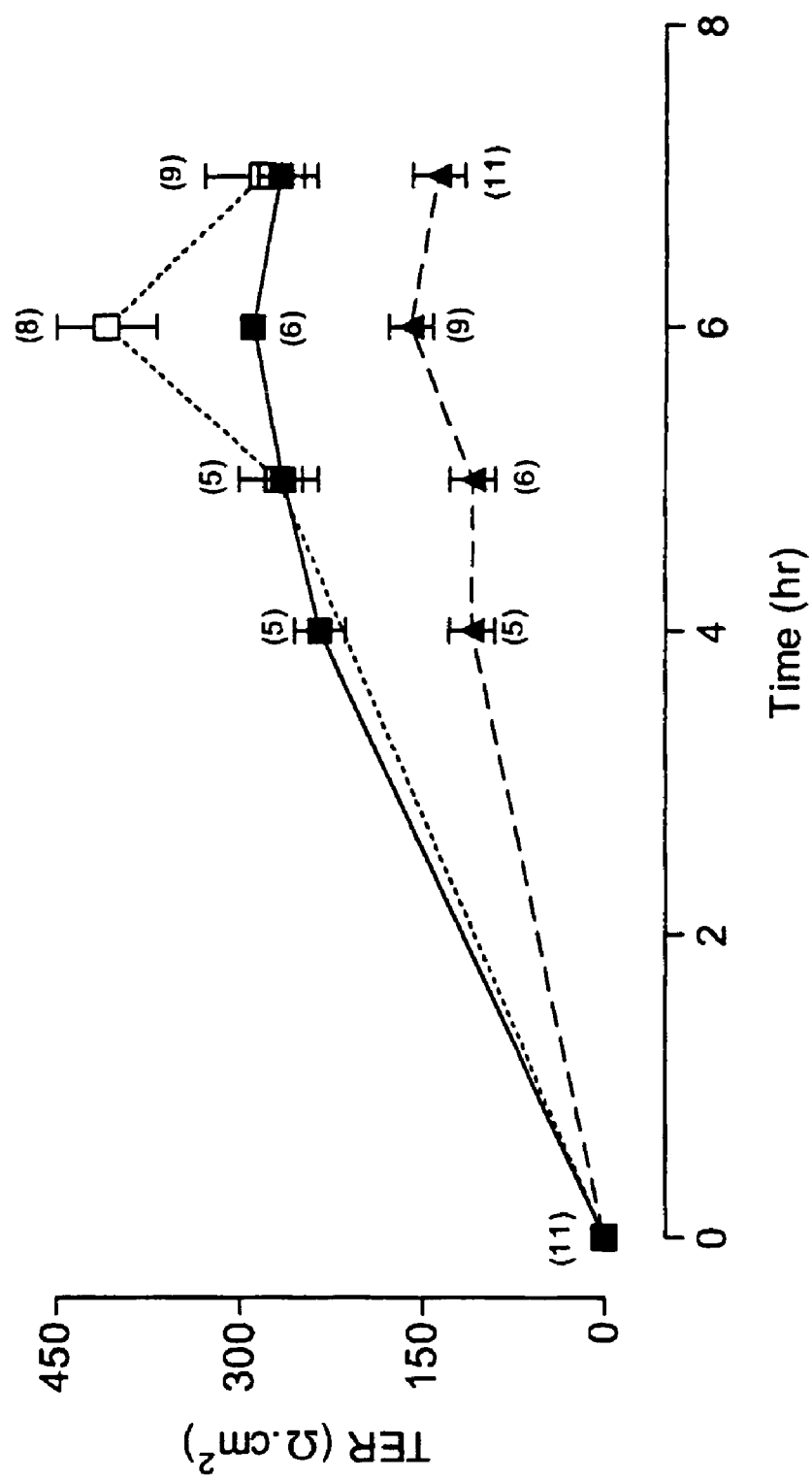

Fig. 7A

1    MASLIYRQLL TNSYTVDLSD EIQEIGSTKT QNVTINLGPF AQTGYAPVNW GPGETNDSTT

61   VEPVLDGPYQ PTSPNPPVDY WMLLAPTAAG VVVEGTNNTD RWLATILVEP NVTSETRSYT

121  LFGTQEQITI AYASQTQWKF IDVVKITQNG SYSQYGPLQS TPKLYAVMKH NGKLYLYNGE

181  TENVTTKLYS TTNYDSVNMT AFCDFYIIPR EEESTCTEYI NNGLPPIQNT R

Fig. 7B

OCCLUDIN

First loop

VP8 peptide:

dog      $_{90}$DRGYGTGLMGGSIGYPYG-SGFGS---YGTGYG--YGFGY-GYGYGGYTDPR$_{134}$
mouse    $_{90}$DRGYGTGLFGGSLNYPY--SGFG----YGGGYGGGYG-GY-GYGYGGYTDPR$_{133}$
rat      $_{90}$DRAYGTGIFGGSMNYPYG-SGFGS---YGGGFGG--YGYGY-GYGYGGYTDPR$_{135}$
human    $_{90}$DRGYGTSLLGGSVGYPYGGSGEGS---YGSGYG--YGYGY-GYGYGGYTDPR$_{135}$
chicken  $_{81}$DYGYG---LGGAYGTGLG-GFYGSNYYGSGLS--YSYGYGGY-YGGVNQRT$_{124}$
kanguroo rat $_{75}$-EYYGS----GGLLGYG----GGLGS---YLNGY--YG

Fig. 7C

| | | | | | | | | | |
|---|---|---|---|---|---|---|---|---|---|
| VP8 | 5 | IYRQLL | 10 | VP8 | 116 | TRSYTL | 121 | | |
| Cl-2 | 66 | IYSTLL | 71 | Cl-11 | 33 | TCSYTI | 38 | VP8 | 202 CDFY 205 |
| Cl-14 | 66 | IYRSLL | 71 | | | | | Cl-2 | 64 CDIY 67 |
| | | | | VP8 | 134 | SQTQWK | 140 | Cl-2 | 145 RDFY 148 |
| VP8 | 18 | LSDEIQ | 23 | Cl-5 | 33 | AQTTWK | 38 | Cl-4 | 145 RDFY 148 |
| Cl-5 | 64 | LSAEVQ | 69 | | | | | Cl-8 | 136 RDFY 139 |
| | | | | VP8 | 142 | VVKTT | 146 | Cl-9 | 145 QDFY 148 |
| VP8 | 27 | STKTQ | 31 | Cl-3 | 31 | VVQST | 35 | Cl-13 | 63 CTLY 66 |
| Cl-13 | 154 | BKKVQ | 158 | Cl-4 | 55 | VVQST | 59 | Cl-17 | 64 CKFY 67 |
| | | | | | | | | Cl-20 | 54 CTWY 57 |
| VP8 | 39 | PFAQTGY | 45 | VP8 | 152 | YSQY | 155 | | |
| Cl-3 | 151 | PEAQ | 154 | Cl-11 | 156 | YSLY | 159 | VP8 | 216 CTEY 219 |
| Cl-15 | 69 | LALSGY | 74 | | | | | Cl-20 | 54 CTWY 57 |
| | | | | VP8 | 155 | YGPL | 158 | | |
| | | | | Cl-1 | 149 | YDPM | 154 | | |
| VP8 | 45 | YAPVN | 81 | Cl-2 | 148 | YSPL | 151 | | |
| Cl-2 | 148 | YSPL | 151 | Cl-3 | 146 | YNPV | 149 | | |
| Cl-3 | 146 | YNPV | 149 | Cl-4 | 148 | YNPM | 151 | | |
| Cl-4 | 148 | YNPM | 151 | Cl-6 | 148 | YNPL | 151 | | |
| Cl-12 | 165 | FEPV | 168 | Cl-7 | 129 | YNPL | 132 | | |
| | | | | Cl-8 | 139 | YNPL | 142 | | |
| VP8 | 65 | LDGPYQ | 70 | Cl-9 | 148 | YNPL | 151 | | |
| Cl-10 | 72 | LDGYIQ | 77 | Cl-14 | 148 | YNPL | 151 | | |
| Cl-19 | 63 | LDGHIQ | 68 | | | | | | |
| | | | | VP8 | 161 | PKLY | 164 | | |
| VP8 | 69 | YQPT | 72 | Cl-14 | 150 | PLLP | 153 | | |
| Cl-2 | 148 | YSPL | 151 | Cl-15 | 160 | PALY | 163 | | |
| Cl-4 | 148 | YNPM | 151 | | | | | | |
| Cl-5 | 139 | YDPT | 143 | VP8 | 170 | HNGKIY | 175 | | |
| | | | | Cl-14 | 57 | HSTGIY | 62 | | |
| VP8 | 74 | FNPPV | 78 | | | | | | |
| Cl-3 | 146 | YNPVV | 150 | VP8 | 173 | KIYTY | 177 | | |
| Cl-4 | 148 | YNPMV | 152 | Cl-1 | 31 | KIYSY | 35 | | |
| Cl-6 | 148 | YNPLV | 152 | | | | | | |
| Cl-7 | 129 | YNPLV | 133 | VP8 | 183 | NVTT | 186 | | |
| Cl-8 | 139 | YNPLV | 143 | Cl-1 | 39 | NIYT | 44 | | |
| Cl-9 | 148 | YNPLV | 152 | | | | | | |
| Cl-14 | 148 | YNPLV | 152 | VP8 | 187 | KYYST | 191 | | |
| | | | | Cl-17 | 65 | KFYSS | 69 | | |
| VP8 | 81 | WMLLA | 85 | | | | | | |
| Cl-16 | 29 | WMVNA | 33 | VP8 | 194 | YDSV | 197 | | |
| | | | | Cl-1 | 65 | YDSL | 68 | | |
| VP8 | 88 | AGVVVEG | 94 | Cl-2 | 67 | YDSM | 70 | | |
| Cl-9 | 43 | AQVVWEG | 49 | Cl-3 | 67 | YDSL | 70 | | |
| | | | | Cl-4 | 67 | YDSL | 70 | | |
| VP8 | 113 | TSETRSYTLFG | 123 | Cl-6 | 67 | YDSL | 70 | | |
| Cl-18 | 167 | TVQTR-YT-FG | 175 | Cl-7 | 64 | YDSI | 67 | | |
| | | | | Cl-8 | 73 | YDSL | 76 | | |
| | | | | Cl-9 | 47 | IDSV | 50 | | |

EMPLOYMENT OF ROTAVIRUS PROTEINS, DERIVED PROTEINS AND PEPTIDES FOR THE MODULATION OF TISSUE PERMEABILITY

RELATED APPLICATIONS

This application is a U.S. National Phase of International Patent application No.: PCT/IB03/00280, filed Jan. 10, 2003, designating the U.S. and published in English as WO 03/098991 on Dec. 4, 2003.

TECHNICAL FIELD

The present invention relates generally to methods for regulating tight junction sealing, and more particularly to the use of proteins and peptides that inhibit cell adhesion and the formation of tissue permeability barriers.

BACKGROUND OF THE INVENTION

The Tight Junction (TJ)

In multicellular organisms fluids with different molecular compositions (urine, milk, gastric juice, blood etc.) are contained in compartments delineated by epithelia (e.g. renal tubules) and endothelia (blood vessels). These cellular sheets constitute the frontier between the organism internal milieu and the compartments' contents. Therefore in order for components of the blood to enter a given tissue, they must first traverse from the lumen of the blood vessel through the endothelial cells of that vessel. In case of substances that enter the body via the gut, they must first pass the barrier formed by the epithelial cells that line the cavity, and to enter the blood via the skin, both epithelial and endothelial sheets must be crossed.

Although cell-cell adhesion is crucial to develop tissues and for maintaining discrete compartments within the organism, there are conditions in which a controlled regulation of cell adhesion is desirable. Such situation is encountered when the barrier formed by the epithelia or endothelia creates difficulties for the delivery of drugs to specific tissues and tumors within the body.

The passage of substances through endothelia and epithelia proceeds through two parallel routes: a transcellular and a paracellular pathway. In the former ions and molecules employ for their transit channels, carriers and pumps located in the plasma membrane of epithelia and endothelia. Attempts to facilitate the passage of drugs to specific tissues within the body have generally relied on such specific channels or carriers that in vivo transport molecules. However such methods have been largely inefficient due to low endogenous transport rates or to their poor functioning with applied drugs.

To overcome these impediments transport through the paracellular pathway has been assayed. This route consists of the intercellular space existent between adjacent cells and is regulated by the tight junction (TJ).

The TJ is a structure that surrounds the cellular borders at the limit between the apical and lateral membranes. It displays two fundamental roles: 1) as a gate that regulates the passage of ions, water and molecules through the paracellular route; and 2) as a fence that blocks the lateral diffusion within the plane of the membrane of lipids and proteins. This fence is crucial since it maintains the polarized distribution of lipids and proteins between the apical and basolateral to plasma membrane (Cereijido et al., 1998).

On ultrathin section electron micrographs, TJ are viewed as a series of fusion points "kisses" between the outer leaflets of the membranes of adjacent cells. At these kissing points, the intercellular space is completely obliterated. On freeze-fracture replica electron micrographs TJ appear at the plasma membrane as a network of continuous and anastomosing filaments on the protoplasmic face (P), with complementary grooves on the exoplasmic face (E) (Gonzalez-Mariscal et al., 2001).

Two models have been proposed to explain the chemical nature of TJ. In the protein model, TJ strands are formed by integral membrane proteins that associate with a partner in the apposing membrane of the adjacent cell. In the lipid model instead, TJ filaments are supposed to be formed of inverted cylindrical micelles (Kachar et al., 1982). Although the lipid content of the bilayer appears to be important for the formation of TJ, the discovery in recent years of TJ specific integral proteins gives strong support to the protein model of TJ.

TJ are constituted by a complex array of cortical and integral proteins. Of the former, 16 different molecules have so far been identified. Some function as scaffolds, that link the integral proteins of the TJ to the actin cytoskeleton (ZO-1, ZO-2, ZO-3 and cingulin) (Citi et al., 1988; Gonzalez-Mariscal et al., 2000), or as crosslinkers of transmembrane junctional proteins (MUPP1, MUPP2 and MUPP3) (Hamazaki et al., 2002). Others are involved in vesicular trafficking to the TJ (Rab13, Rab3b) (Zahraoui et al., 1994), in cell signaling through their association to kinases (Par3 and Par 6) (Izumi et al., 1998) and Ras (e.g. AF6) (Yamamoto et al., 1997), and in gene expression by their specific binding to transcription factors (ZO-1 and ZO-2) (Balda et al., 2000). The role of several other cortical proteins found at the TJ still remains unclear [e.g. Jeap (Nishimura et al., 2002), Pilt (Kawabe et al., 2001), Barmotin (Zhong et al., 1993) and symplekin (Keon et al., 1996)].

At the TJ three integral proteins are found: occludin, claudins and JAM. Occludin was the first one identified (Furuse et al., 1993). It is considered a component of TJ strands, since immuno replica electron microscopy with specific antibodies revealed its labeling within the TJ filaments (Saitou et al., 1997). Furthermore, when introduced into L fibroblasts, that lack TJ, structures that resemble TJ strands were formed.

Occludin comprises four transmembrane regions, two extracellular loops of similar size, and three cytoplasmic domains: one intracellular short turn, a small amino terminal domain and a long carboxyl terminal region.

Several lines of evidence assign occludin an important role at TJ. Thus, the over-expression of mutant forms of this protein in epithelial cells leads to changes in the barrier and fence function of TJ (Balda et al., 1996b; McCarthy et al., 1996) (Bamforth et al., 1999) and in the transepithelial migration of neutrophils (Huber et al., 2000). (Lacaz-Vieira et al., 1999). (Medina et al., 2000) (Vietor et al., 2001) Additionally, a correlation has been observed in several tissues between the expression of occludin and the degree of sealing of epithelia evaluated by transepithelial electrical resistance (TER) and permeability to extracellular tracers. Despite this evidence the physiological function of occludin is not completely understood. In this regard it should be highlighted that embryonic cells and mice carrying a null mutation in the occludin gene are still able to form well developed TJ (Saitou et al., 1998), although the animals display postnatal growth retardation and histological abnormalities in several tissues (Saitou et al., 2000).

More recently other integral proteins named claudin 1 and claudin 2 were identified as TJ constituents. By data base searching and cDNA and genomic cloning the claudin family has expanded to 20 members (Tsukita et al., 2001). All claudins encode 20 to 27 kDa proteins with four transmembrane domains; two extracellular loops where the first one is significantly longer than the second one, and a short carboxyl intracellular tail.

When claudins were transfected into fibroblasts, they conferred cell-cell aggregation activity, concentrated at the cells contact points and formed networks of filaments that looked like TJ strands. Furthermore, in immunoreplica electron microscopy antibodies against different claudins selectively labeled the TJ filaments of epithelia. All this evidence has let to consider claudins as the backbone of TJ strands.

Different claudin species are capable of generating different freeze fracture patterns. Thus, claudins 1 or 3 form TJ with continuous smooth fibrils on the protoplasmic surface (P face) of the replicas (Furuse et al., 1999), whereas claudins 2 or 5 generate junctions with discontinuous chains of particles associated to the exoplasmic face (E face) (Morita et al., 1999b). Claudin 11 instead constitutes parallel TJ strands on the P face that scarcely branch (Morita et al., 1999a).

Heterogeneous claudins can interact within a single TJ strand and their particular combination gives rise to different freeze fracture patterns. Thus strands formed with claudins 1 and 3 are continuous and associated to the P face, while strands formed with claudins 1 and 2 or 3 and 2 have evenly scattered particles in the E face grooves. At the paracellular space the extracellular loops of different species of claudins belonging to neighboring cells can also interact, except in some combinations (Furuse et al., 1999).

The expression of different claudins in epithelia and endothelia might give rise to the ample variety in permeability and paracellular ionic selectivity displayed in distinct tissues. The nephron that displays a wide range of TER along the different tubular segments (6 $\Omega cm^2$ in proximal Vs 870-2000 $\Omega cm^2$ in collecting duct) expresses almost all claudins, yet each one is restricted to a particular segment (Enck et al., 2001; Kiuchi-Saishin et al., 2002) (Reyes et al., 2002): claudins 5 and 15 at endothelia, claudins 2, 10 and 11 at the proximal segment, claudins 1, 3 and 8 at de distal tubule and claudins 1, 3, 4 and 8 at the collecting segment.

The onset of expression for different claudins is developmentally regulated. Thus, claudin 5 is transiently expressed during the development of the retinal pigment epithelium (Kojima et al., 2002), claudin 11 is expressed in Sertoli cells, immediately after the peak of expression of the sex determining region in the Y gene (Hellani et al., 2000), and claudin 6 is found in embryonic stem cells committed to the epithelial fate (Turksen et al., 2001).

Claudin 16 is mutated in human patients with hypomagnesemia hypercalciuria syndrome (HHS) (Simon et al., 1999). These patients manifest a selective defect in paracellular $Mg^{2+}$ and $Ca^{2+}$ reabsorption in the thin ascending limb of Henle's, with intact NaCl resorption ability at this site (Blanchard et al., 2001). Therefore claudin 16 appears to function as a paracellular channel selective for $Mg^{2+}$ and $Ca^{2+}$ (Goodenough et al., 1999). Other claudins are also proved ionic selective. Thus when claudin 4 is transfected into epithelial cells, the paracellular conductance decreases through a selective decrease in $Na^+$ permeability without a significant effect on $Cl^-$ permeability (Van Itallie et al., 2001).

More than two decades ago Claude observed that the TER increases with the number of TJ strands, not in a linear fashion as would be expected from the addition of resistors in series, but exponentially (Gonzalez-Mariscal et al., 2001). To explain this relationship a proposal arose suggesting the existence of ion channels or pores within the TJ strands (Claude 1978; Gonzalez-Mariscal et al., 2001). Now that claudins have begun to be characterized, it appears that the ionic selectivity at the TJ could be determined by the specific claudin isoforms that constitute the pores or channels of TJ strands.

On analyzing the extracellular loops of claudins an enormous variability in distribution and number of charged residues is found. For example the isoelectric points of the first loop range from 4.17 in claudin 16 to 10.49 in claudin 14, and in the second extracellular loop from 4.05 in claudins 2, 7, 10 and 14 to 10.5 in claudin 13. Based on the pKIs of the extracellular loops sequences, claudin 16 is a cation pore, a proposal that agrees with the observed effect of its mutation in human patients, whereas claudins 4, 11 and 17 are anion pores (Mitic et al., 2001).

Variations in the tightness of the TJ appear to be determined by the combination and mixing ratios of different claudin species. Thus when MDCK cells expressing claudin 1 and 4 were incubated with a claudin 4 binding peptide (Clostridium perfringens enterotoxin, CPE), claudin 4 was selectively removed from TJ, generating a significant decrease in TER (Sonoda et al., 1999). Furthermore, when claudin-2 was introduced into high resistance MDCK cells (MDCK I), TJ became leaky and morphologically similar to those found in low resistance cells (MDCK II), which normally contain claudin 2 (Furuse et al., 2001).

The role of claudins in carcinogenesis is controversial. Claudin 4 is over-expressed in pancreatic cancer and gastrointestinal tumors, and the treatment with TGFβ or CPE, the enterotoxin that specifically targets claudin 4, leads to a significant reduction of tumor growth (Michl et al., 2001). In contrast, other claudins remain low or undetectable in a number of tumors and cancer cell lines. For example Claudin 1 expression is lost in most human breast cancers without presenting alterations in its promoter or coding sequences (Hoevel et al., 2002; Kramer et al., 2000), and claudin 7 is down-regulated in head and neck squamous cell carcinomas (Al Moustafa et al., 2002).

The crucial role of certain claudins in the gate function of epithelia is highlighted by the observation that in claudin 1 deficient mice the epidermis looses it barrier function, leading to dehydration of the animals, wrinkled skin and death within 1 day of birth (Furuse et al., 2002). In these mice occludin was still expressed at all layers of the stratified epithelia, and claudin 4 remained concentrated at the second and third layers of the stratum granulosum. Therefore in the epidermis claudin-1 constitutes an indispensable element for the barrier function of TJ.

The last integral proteins of the TJ are JAM and the three JAM like proteins (Palmeri et al., 2000). They belong to the immunoglobulin superfamily, have a single transmembrane segment and their extracellular portion consists of two folded immunoglobulin like domains. JAM appears not to be a constituent of TJ strands since its transfection into fibroblasts does not generate the appearance of filaments. JAM plays a role in cross-linking occludin and claudins, as well as in the transepithelial and transendothelial migration of monocytes (Martin-Padura et al., 1998).

Physiological and Pathological Regulation of Tight Junctions.

Epithelia and endothelia encounter diverse physiological and pathological conditions that provoke changes in the degree of sealing of TJ. These variations in TJ permeability are regulated by a broad spectrum of factors such as calcium (Gonzalez-Mariscal et al., 1990; Martinez-Palomo et al., 1980), hormones, cytokines and growth factors, activation of G proteins and phospholipases, generation of CAMP and diacylglicerol (Balda et al., 1991), and by the phosphorylation of TJ proteins by different kinases (Avila-Flores et al., 2001; Balda et al., 1996a; Sakakibara et al., 1997).

In recent years the action of enteric pathogens (e.g. *Escherichia coli, Salmonella typhimurium*) and bacterial toxins upon TJ has been recognized (Hecht2002). Thus, treatment with *Clostridium perfringens* enterotoxin (CPE) destroys TJ and TER by specifically removing claudins 3 and 4 from the strands (Sonoda et al., 1999), while the hemaglutinin and ZOT toxin of Vibrio cholera increase epithelial permeability due to their respective action upon occludin (Wu et al., 2000) and PKC (Fasano et al., 1995). From an evolutionary point of view, bacteria that counted with toxins that mimicked endogenous modulators of TJ were in advantage since by traversing epithelial barriers they gained access to new environments. This appears to be the case for Vibrio cholera, as an endogenous protein that modulates TJ has been recently identified employing antibodies generated against ZOT toxin (Fasano1999; Wang et al., 2000).

Rotaviruses

Rotaviruses are the leading cause of morbidity and mortality caused by gastroenteritis in children less than 2 years old. These viruses of the Reoviridae family have a genome composed of 11 double stranded segments of RNA, surrounded by three concentric layers of protein. The outermost layer is smooth and formed by a 37 kDa glycoprotein named VP7. From it around 60 spikes formed of an 88 kDa protein named VP4, project outwards (Estes1996).

VP4 is essential for early virus-cell interactions, since it participates in receptor binding and cell penetration. In fact the infectivity of rotaviruses is dependent upon the specific cleavage by trypsin of VP4 into peptides VP5 and VP8 (Almeida et al., 1978; Espejo et al., 1981).

In vivo rotavirus infection is restricted to ileum microvellosities (Kapikian et al., 1996). In vitro infectiveness is less restrictive as a broad variety of renal and intestinal epithelial cell lines are susceptible to rotavirus infection (Estes et al., 1989).

Some rotaviruses bind to a cell-surface receptor containing sialic acid (SA), while others (e.g. human rotavirus) do not require SA for infection (Fukudome et al., 1989). Therefore binding to SA appears not to be an essential step for rotavirus infection. Furthermore, association to a secondary SA independent receptor can overcome the initial interaction of certain rotavirus with SA. SA dependent rhesus rotavirus (RRV) initially bind to the cell through VP8 (Fiore et al., 1991; Isa et al., 1997), while variants of RRV which no longer depend on the presence of SA (e.g. nar3), interact with the cell through VP5 (Zarate et al., 2000b). The comparative characterization of many strains of animal and human origin, including RRV, its SA independent variant nar3, and the human rotavirus strain Wa, has shown that rotavirus contain integrin ligand sequences (Coulson et al., 1997) (Guerrero et al., 2000) and that $\alpha_2\beta_1$ integrin is used as a primary cell receptor by nar3, and by RRV in a secondary interaction, subsequent to its initial contact with the SA containing cell receptor (Zarate et al., 2000a). Integrin $\alpha V\beta_3$ is used by all three rotavirus strains as a co-receptor, subsequent to their initial attachment to the cell (Guerrero et al., 2000). Integrins $\alpha X\beta_2$ and $\alpha_4\beta_1$ have also been suggested to participate in rotavirus cell entry (Coulson et al., 1997; Hewish et al., 2000).

Aside of their function as cellular receptors for viruses, integrins constitute a family of $\alpha\beta$ heterodimers that mediate the interaction between the cell and the extracellular matrix. This interaction plays a crucial role in the regulation of cell no proliferation, migration and differentiation. In epithelial and endothelial cells integrins have a polarized distribution and localize at the basolateral plasma membrane. Therefore rotaviruses contained in the lumen of the intestine or at the apical surface of confluent epithelial cell lines could only have access to their integrin receptors at the basolateral surface if the TJ that seal the paracellular route are opened.

Since as stated at the beginning of this description, there is a need in the art for compounds that modulate junctional tightness and improve drug delivery across permeability barriers, we proceeded to explore the capacity of rotavirus proteins to modulate TJ sealing. The present invention fulfills this need and provides other related advantages. Recently, cell transformation has been correlated with over expression of certain claudins (Michl et al., 2001). Therefore the rotavirus proteins and derived peptides that target junctional proteins could also be employed for reducing tumor cell growth.

In the present invention we have worked with proteins and peptides derived from the VP4 molecule of Rhesus monkey rotavirus (RRV). Rotavirus infect a wide variety of vertebrates, such as chickens, horses, pigs, monkeys and humans, and several strains of viruses have been isolated from different individuals of the same specie. However, since the amino acid sequence of VP4 maintains a high degree of identity among most of the different rotavirus strains, it is expected that the different strains independent of their origin will exert a similar effect upon TJ. In consequence in the present invention we will further refer to VP4 and its derived peptides, without placing special emphasis on their origin.

SUMMARY OF THE INVENTION

The present invention provides proteins, peptides and methods for modulating tight junction mediated cell-cell adhesion and the formation of permeability barriers.

One aspect of the present invention is the use of rotavirus protein VP4, its derived polypeptide VP8, or peptides derived from them, to induce the opening of tight junctions.

Another aspect of the present invention is the use of rotavirus protein VP4 or its derived polypeptide VP8 or peptides derived from them to increase the paracellular permeability of epithelia and endothelia.

One crucial aspect of the present invention is the use of the rotavirus protein VP4, of the derived polypeptide VP8, or of peptides from them derived to allow and/or to enhance the passage of therapeutical agents through the paracellular pathway.

One additional aspect of the present invention is the use of rotavirus protein VP4, its derived polypeptide VP8, or peptides derived from them, to modulate and/or enhance the passage of therapeutical agents through the intestinal, nasal, ocular, vaginal and rectal epithelium.

A further objective of the present invention is the use of rotavirus protein VP4, its derived polypeptide VP8, or peptides derived from them, to allow and/or to enhance the passage of dermatological agents.

Within another aspect of the present invention, is the use of rotavirus protein VP4, its derived polypeptide VP8, or peptides derived from them, to allow and/or to enhance the passage of therapeutical agents across the blood-brain barrier.

Within a further aspect of the present invention, is to enhance the delivery of a drug to a tumor in a mammal, comprising administering the rotavirus protein VP4, its derived polypeptide VP8 or peptides derived from them, in combination with a drug to a tumor-bearing mammal.

The present invention further provides pharmaceutical compositions comprising rotavirus protein VP4, its derived polypeptide VP8 or peptides derived from it in combination with a pharmaceutically acceptable carrier. Such compositions may further comprise a drug. In addition, or alternatively, such compositions may comprise one or more of: a)

peptides that modulate tight and/or adherens junctions; and/or b) an antibody or antigen binding fragment that specifically binds to TJ proteins.

Within further aspects, the present invention proposes the use of rotavirus protein VP4, its derived polypeptide VP8 or peptides derived from it, for treating cancer in mammals, where epithelial transformation is related to over expression of tight junction proteins.

Within a related aspect of the present invention rotavirus protein VP4, its derived polypeptide VP8, or peptides derived from it, might be employed to treat cancer and/or inhibit metastasis, by disrupting the growth of new capillaries that constitute a prerequisite for tumor growth and the emergence of metastases.

Within another related aspect of the present invention, protein VP4, its derived polypeptide VP8, or peptides derived from them can be used to reduce unwanted cellular adhesion that can occur between tumor cells, tumor cells and normal cells or between normal cells as a result of surgery, injury, chemotherapy, disease, inflammation or other condition jeopardizing cell viability or function.

One preferent form of the invention consists in the use of protein VP4, with ID SEQ. 1

Another preferent form of the invention consists in the use of polypeptide VP8, with ID SEQ. 2.

Yet another preferent form of the invention is centered on the use of fragment 141 to 182 of VP8 with ID SEQ 3:

$_{141}$IDVVKTTQNGSYSQYGPLQSTPKLYGVMKHNGKIYTYNGETP$_{182}$

Even another preferent form of the invention is the use of one or more of the following peptides derived from VP4:

Peptide SEQ. ID 4: $_{144}$VVKT$_{147}$
Peptide SEQ. ID 5: $_{151}$SYSQYGPL$_{158}$
Peptide SEQ. ID 6: $_{174}$IYTY$_{177}$
Peptide SEQ. ID 7: $_{13}$NVTT$_{186}$ Such peptides can be without limitations either cyclic (include a Cys on each of their terminal ends) or linear.

These and other aspects of the invention will become evident upon reference to the following detailed description and attached drawings.

BRIEF DESCRIPTION OF DRAWINGS

FIG. 4. VP8 modifies the pattern distribution of the TJ proteins ZO-1, occludin and claudin-3. Confluent MDCK monolayers were incubated in media with 4 µg/ml of VP8. After one hour, the monolayers were fixed and processed for immunofluorescence with specific antibodies against ZO-1, occludin, claudin-3. Arrowheads indicate the clear distribution of ZO-1, occludin and claudin-3 at the cellular boundaries of control monolayers. In GST-VP8 treated cells, ZO-1 displays a strong immunoreactivity in the cytoplasm (arrow), claudin-3 cell border staining becomes barely detectable in large areas of the monolayer (arrow) and occludin sharp staining is substituted for a diffuse and wide label at the cellular boundaries (arrow).

Figure 1:
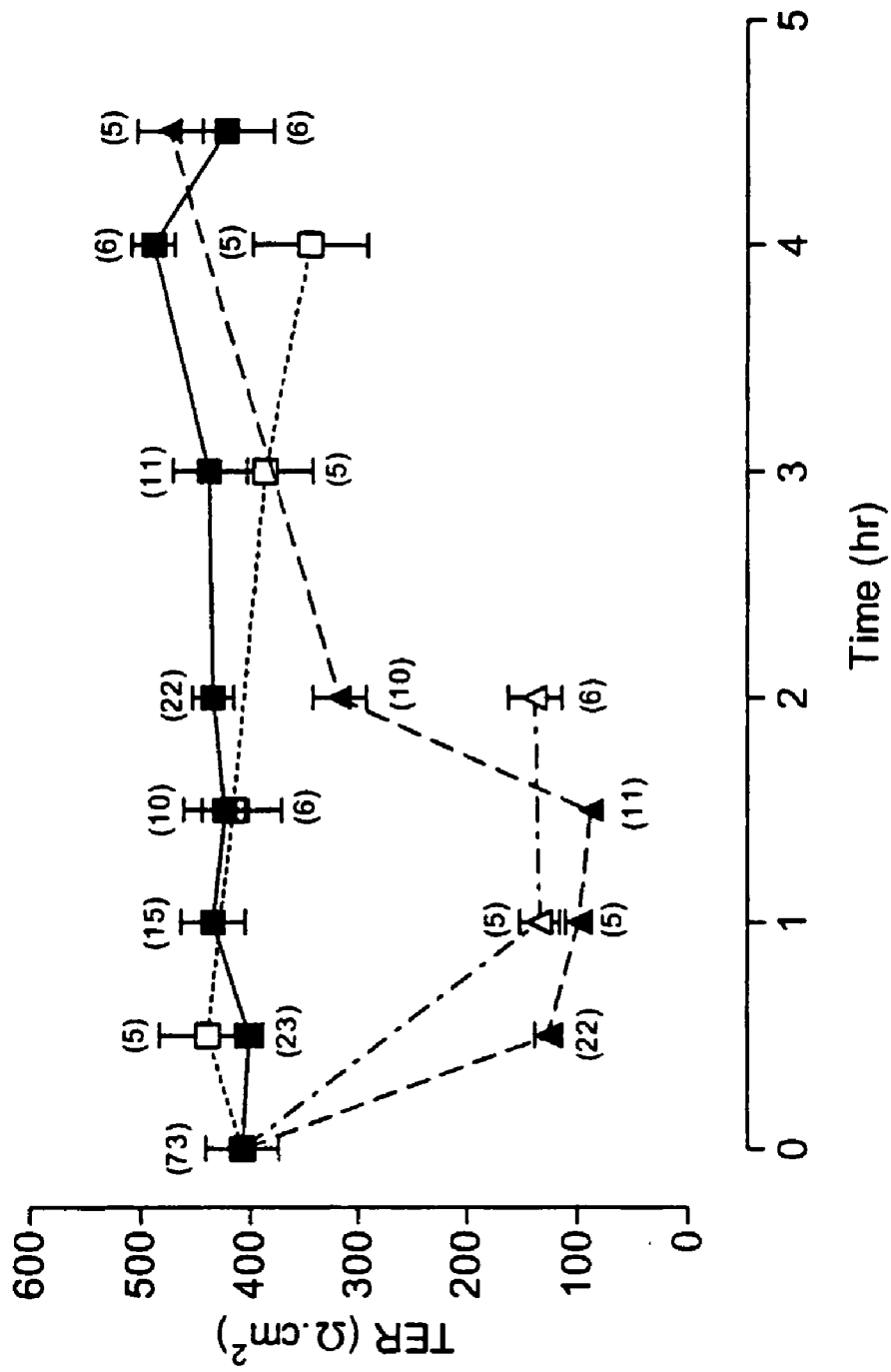
FIG. 1. Viral protein VP8 diminishes the TER of epithelial monolayers (MDCK) in a reversible manner. TER was determined in control MDCK monolayers (full squares) and in those receiving 4 µg/ml of VP5 (empty squares), GST-VP8 (full triangles) or His-VP8 (empty triangles). In this and the following figures the experimental values shown correspond to the media±standard error. The number of independent measurements is indicated at each experimental point.
Figure 2:
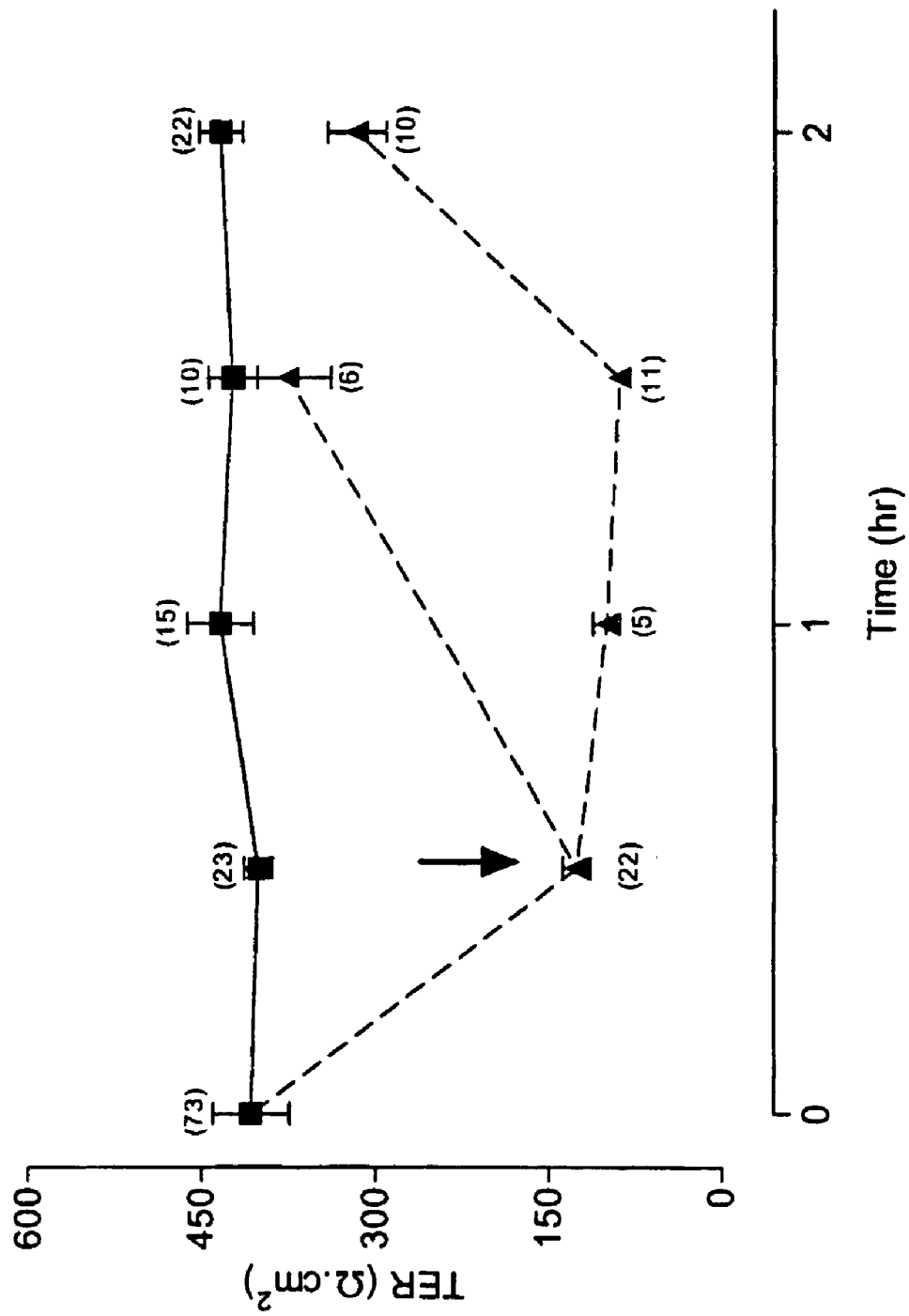
FIG. 2. Monolayers recover their TER when VP8 is withdrawn from the culture media. Monolayers that receive 4 µg/ml of GST-VP8 display a significant decrease in TER (full triangle). However, if the monolayers are washed and transferred to media without GST-VP8 (arrow) they recover their TER. (Full squares=monolayers cultured in media without VP8).
Figure 3:
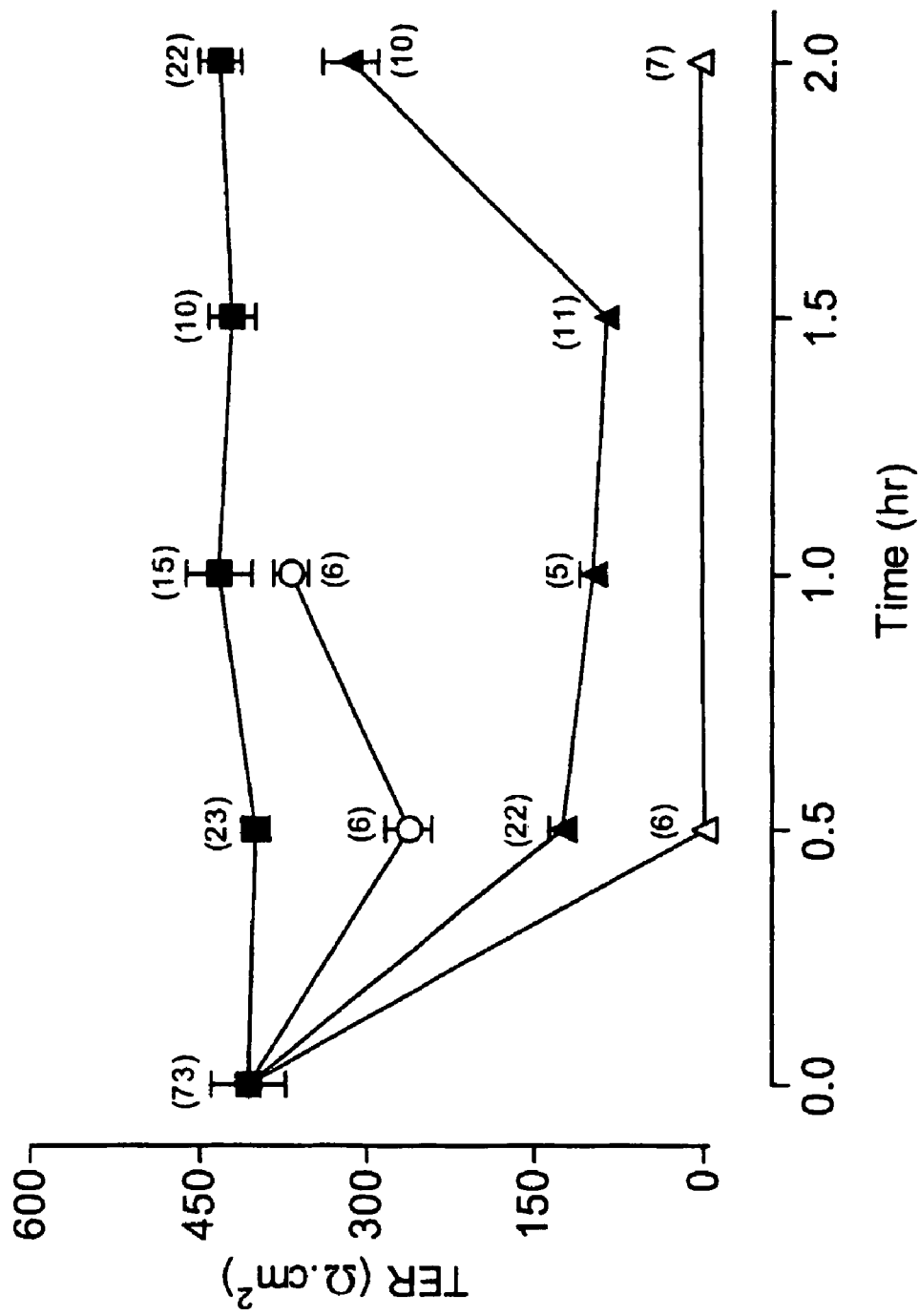
FIG. 3. The effect of VP8 upon TER is dose dependent. MDCK monolayers incubated with 0.4 (empty circles), 4 (full triangles) or 10 µg/ml (empty triangles) GST-VP8 show a dose-dependent decrease in TER.

Arrowheads indicate the clear distribution of ZO-1, occludin and claudin-3 at the cellular boundaries of control monolayers. Arrowheads point to the diffuse staining of ZO-1, occludin and claudin-3 that appears near the cellular borders of VP8 treated monolayers.

FIG. 5. Freeze-fracture analysis of the TJ present in MDCK monolayers treated with VP8. Confluent MDCK monolayers incubated or not with 4 µg/ml VP8 were fixed and processed for freeze-fracture, according to standard procedures. (a) shows representative images of control (A) and VP8 treated monolayers (B). In the latter several loose ends (arrowheads) are found between regions where the network is profound and complex (asterisks). P=protoplasmic face; E=exoplasmic face; bar=200 nm. (b) shows the morphometric analysis of TJ. 1,239 and 1,124 TJ sites were analyzed for the control (lighter bars) and VP8 treated monolayers (darker bars) respectively.

FIG. 6. VPB inhibits the development of TER in epithelial monolayers. Confluent MDCK monolayers cultured in low calcium media (1-5 µM Ca$^{2+}$) develop their TER upon transfer to normal calcium media (1.8 mM Ca$^{2+}$) (full squares). If the monolayers are transferred to normal calcium media containing 4 µg/ml of VP5 (empty squares) the resistance develops as in the control condition. If instead the monolayers are cultured in normal calcium media containing 4 µg/ml of VP8 (full triangle) a clear inhibition in the development of TER is detected.

FIG. 7. The sequence of VP8 contains several regions highly similar to occludin and claudins segments present in their external loops.

(A) The shadowed segments of VP8 sequence (SEQ ID NO:2) have a ≧50% identity to regions of the extracellular loops of occludin or claudin. Next to the brackets the name of the similar protein is indicated (e.g. cl 2, occl etc.). The sequence of peptide VP8$_{141-182}$ is indicated within a frame. (B) Sequence comparison of VP8$_{150-159}$ (SEQ ID NO: 8) and VP8$_{174-177}$ (SEQ ID NO: 6) with occludin external loops. First Loop: Dog, (SEQ ID NO: 9); mouse, (SEQ ID NO:10); rat, (SEQ ID NO:11); human, (SEQ ID NO:12); chicken, (SEQ ID NO:13); and kangaroo rat, (SEQ ID NO:14). Second Loop: Dog, (SEQ ID NO:15); mouse, (SEQ ID NO:16); rat, (SEQ ID NO:17); human, (SEQ ID NO:18); chicken, (SEQ ID NO:19); and kangaroo rat, (SEQ ID NO:20). (C) Sequence comparison between diverse VP8 segments and claudins.

VP8 Segments: 5-10, (SEQ ID NO: 21); 18-23, (SEQ ID NO: 22); 27-31, (SEQ ID NO: 23); 39-45, (SEQ ID NO: 24); 45-49, (SEQ ID NO: 25); 65-70, (SEQ ID NO: 26); 69-72, (SEQ ID NO: 27); 74-78, (SEQ ID NO: 28); 81-85, (SEQ ID NO: 29); 88-94, (SEQ ID NO: 30); 113-123, (SEQ ID NO: 31); 116-121, (SEQ ID NO: 32); 134-140, (SEQ ID NO: 33); 142-146, (SEQ ID NO: 34); 152-155, (SEQ ID NO: 35); 155-158, (SEQ ID NO: 36); 161-164, (SEQ ID NO: 37); 170-175, (SEQ ID NO: 38); 173-177, (SEQ ID NO: 39); 183-186, (SEQ ID NO: 40); 187-191, (SEQ ID NO: 41); 194-197, (SEQ ID NO: 42); 202-205, (SEQ ID NO: 43); 216-219, (SEQ ID NO: 44);

C1-1 Segments: 149-154, (SEQ ID NO: 45); 31-35, (SEQ ID NO: 46); 39-44, (SEQ ID NO: 47); 65-68, (SEQ ID NO: 48);

C1-2 Segments: 66-71, (SEQ ID NO: 49); 148-151, (SEQ ID NO: 50); 67-70, (SEQ ID NO: 51); 64-67, (SEQ ID NO: 52); 145-148, (SEQ ID NO: 53);

C1-3 Segments: 151-154, (SEQ ID NO: 54); 146-149, (SEQ ID NO: 55); 146-150, (SEQ ID NO: 56); 31-35, (SEQ ID NO: 57); 67-70, (SEQ ID NO: 58);

C1-4 Segments: 148-151, (SEQ ID NO: 59); 148-152, (SEQ ID NO: 60); 55-59, (SEQ ID NO: 61); 67-70, (SEQ ID NO: 62); 145-148, (SEQ ID NO: 63);

C1-5 Segments: 64-69, (SEQ ID NO: 64); 139-143, (SEQ ID NO: 65); 33-38, (SEQ ID NO: 66);

C1-6 Segments: 148-152, (SEQ ID NO: 67); 148-151, (SEQ ID NO: 68); 67-70, (SEQ ID NO: 69);

C1-7 Segments: 129-133, (SEQ ID NO: 70); 129-132, (SEQ ID NO: 71); 64-67, (SEQ ID NO: 72);

C1-8 Segments: 139-143, (SEQ ID NO: 73); 139-142, (SEQ ID NO: 74); 73-76, (SEQ ID NO: 75); 136-139, (SEQ ID NO: 76);

C1-9 Segments: 148-152, (SEQ ID NO: 77); 43-49, (SEQ ID NO: 78); 148-151, (SEQ ID NO: 79); 47-50, (SEQ ID NO: 80); 145-149, (SEQ ID NO: 81);

C1-10 Segments: 72-77, (SEQ ID NO: 82);

C1-11 Segments: 33-38, (SEQ ID NO: 83); 156-159, (SEQ ID NO: 84);

C1-12 Segments: 165-168, (SEQ ID NO: 85);

C1-13 Segments: 154-158, (SEQ ID NO: 86); 63-66, (SEQ ID NO: 87);

C1-14 Segments: 66-71, (SEQ ID NO: 88); 148-152, (SEQ ID NO: 89); 148-151, (SEQ ID NO: 90); 150-153, (SEQ ID NO: 91); 57-62, (SEQ ID NO: 92);

C1-15 Segments: 69-74, (SEQ ID NO: 93); 160-163, (SEQ ID NO: 94);

C1-16 Segments: 29-33, (SEQ ID NO: 95);

C1-17 Segments: 65-69 (SEQ ID NO: 96); 64-67, (SEQ ID NO: 97);

C1-18 Segments: 167-175, (SEQ ID NO: 98),

C1-19 Segments: 63-68, (SEQ ID NO: 99); and

C1-20 Segments: 54-57, (SEQ ID NO: 100).

The shadowed letters correspond to amino acids in VP8 that are identical to those present in claudins. The sequence access number for the different claudins employed are: claudin 1, rat, NP113887; claudin 2, dog, AAK57433; claudin 3, rat, NP113888; claudin 4, mouse, NP034033; claudin 5, rat, AAF73425; claudin 6, mouse, Q9Z262; claudin 7, rat, CAA09790; claudin 8, mouse, Q9Z260; claudin 9, mouse, NP064689; claudin 10, mouse, Q9Z056; claudin 11, rat, NP445909; claudin 12, human, XP004591; claudin 13, mouse, Q9Z054; claudin 14, mouse, NP062373; claudin 15, mouse, NP68365; claudin 16, rat, NP571980; claudin 17, human, P56750; claudin 18, mouse, P56857; claudin 19, mouse, AAF98323; claudin 20, human P56880.

Figure 8:
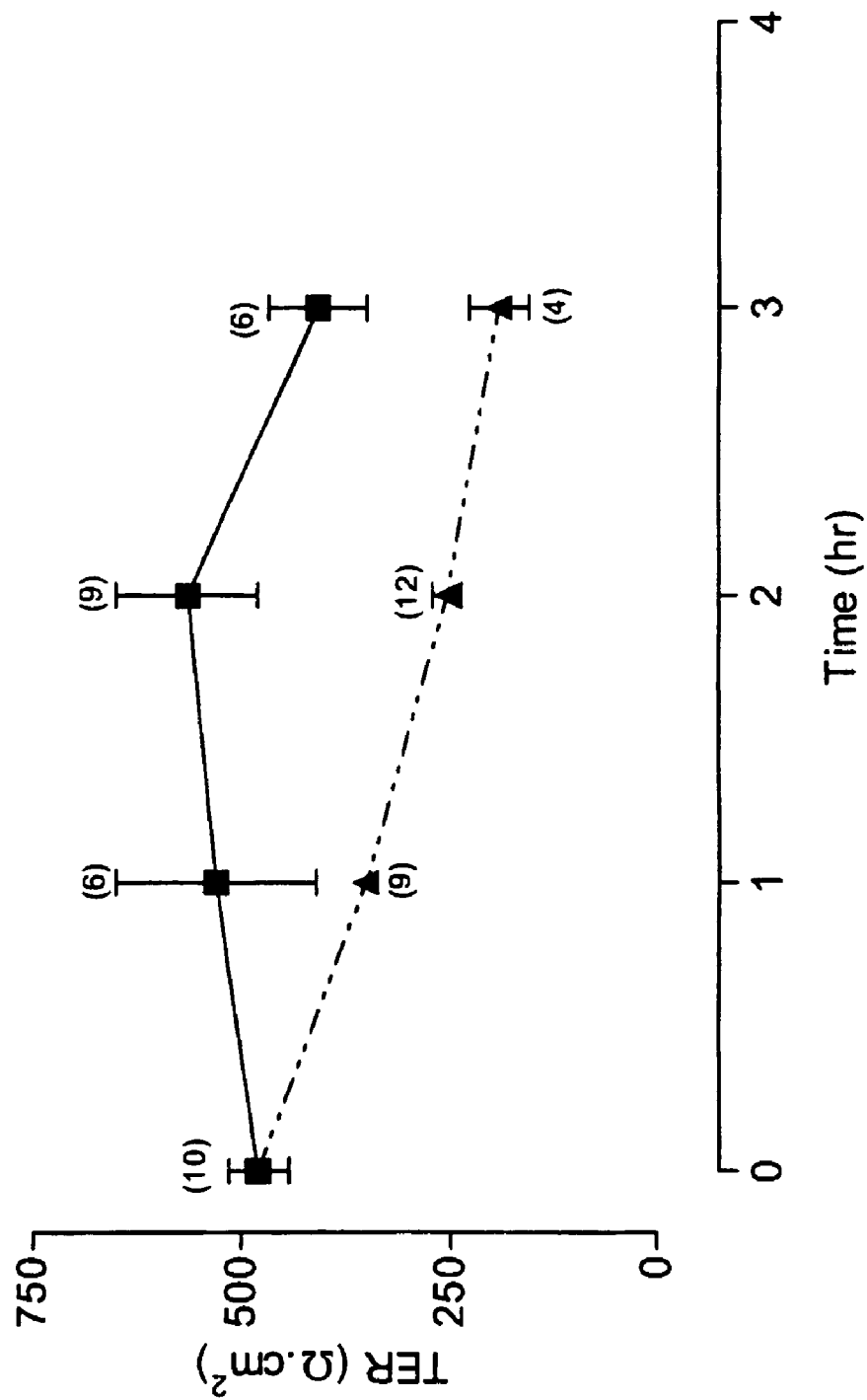

FIG. 8. Addition of peptide His-VP8$_{141-182}$ reduces the TER of epithelial monolayers. Confluent MDCK monolayers treated with 4 µg/ml of peptide His-VP8$_{141-182}$ (full triangles) show a significant reduction in TER compared to monolayers treated with His elution buffer only (full squares).

Figure 9:
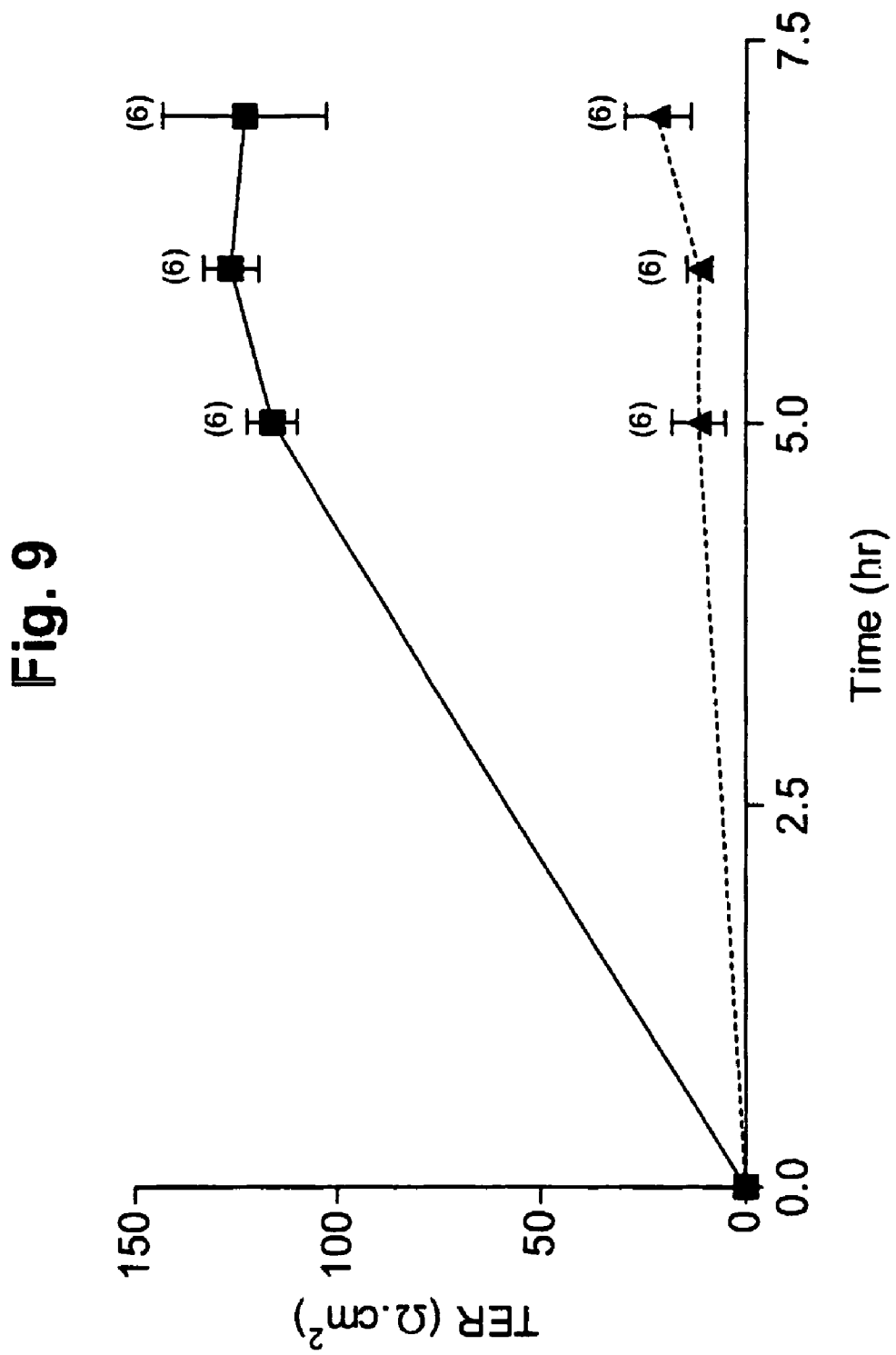

FIG. 9. Addition of peptide VP8$_{141-182}$ (SEQ. ID. No. 3) inhibits the development of TER in epithelial monolayers. Confluent MDCK monolayers cultured in low calcium media (1-5 µM Ca$^{2+}$) develop their TER upon transfer to normal calcium media (1.8 mM Ca$^{2+}$) (full squares). If instead the monolayers are transferred to normal calcium media containing 4 µg/ml of peptide VP8$_{141-182}$ (full triangles) a clear inhibition in the development of TER is detected.

Figure 10:
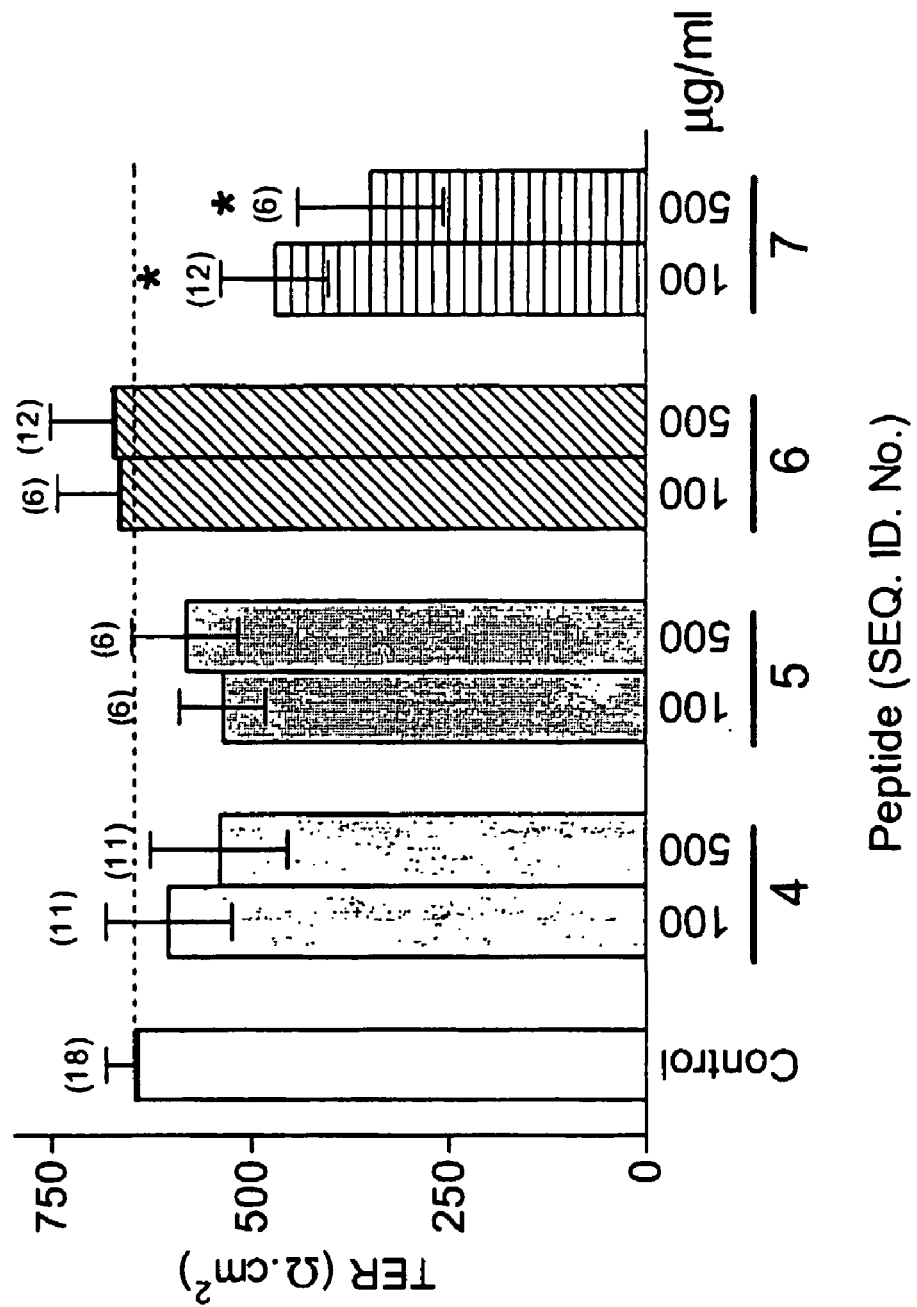

FIG. 10. The addition of peptides SEQ. ID. No 7 reduces the TER of epithelial monolayers. Confluent MDCK monolayers were treated with peptides SEQ. ID. No. 4, 5, 6 or 7 at a concentration of 100 or 500 µg/ml. While the monolayers incubated in the presence of peptides SEQ. ID. No 4, 5 or 6 display a TER similar to that of control cultures (dashed line), those treated with peptide No 7 show a significantly lower TER ($P<0.05$ in a Student-t test).

Figure 11:
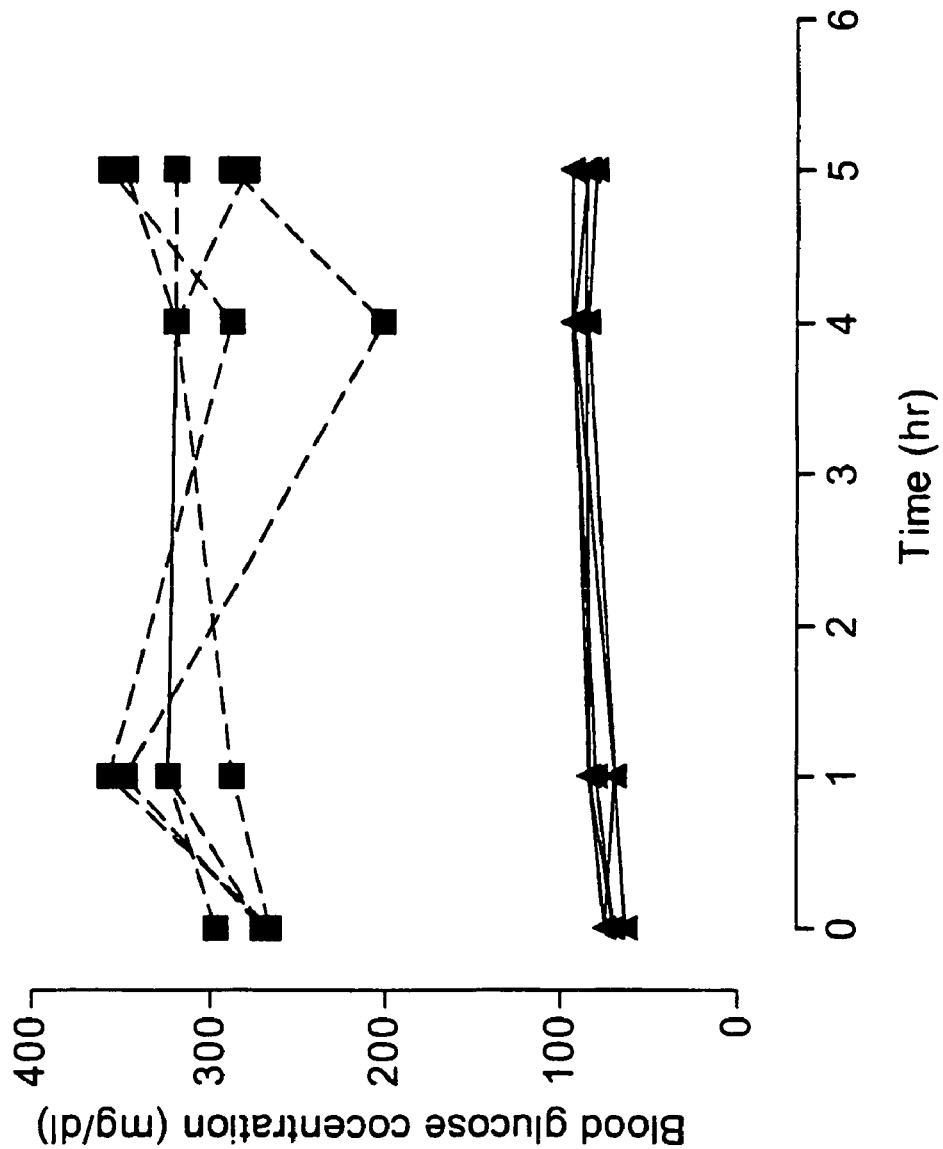

FIG. 11. Streptozotocin significantly increases the concentration of blood glucose in rats. Glucose concentration was determined from a blood sample obtained from the eye orbital sinus of male Wistar rats. The experiment was performed three days after the rats received an intraperitoneal injection of streptozotocin (75 mg/kg of body weight) (dashed lines) or a mock injection (continuous lines). In this and the following figures, blood samples were taken after overnight fasting (time=0) or at different times after the animals received their diet. Each line corresponds to the results obtained with one animal.

Figure 12:
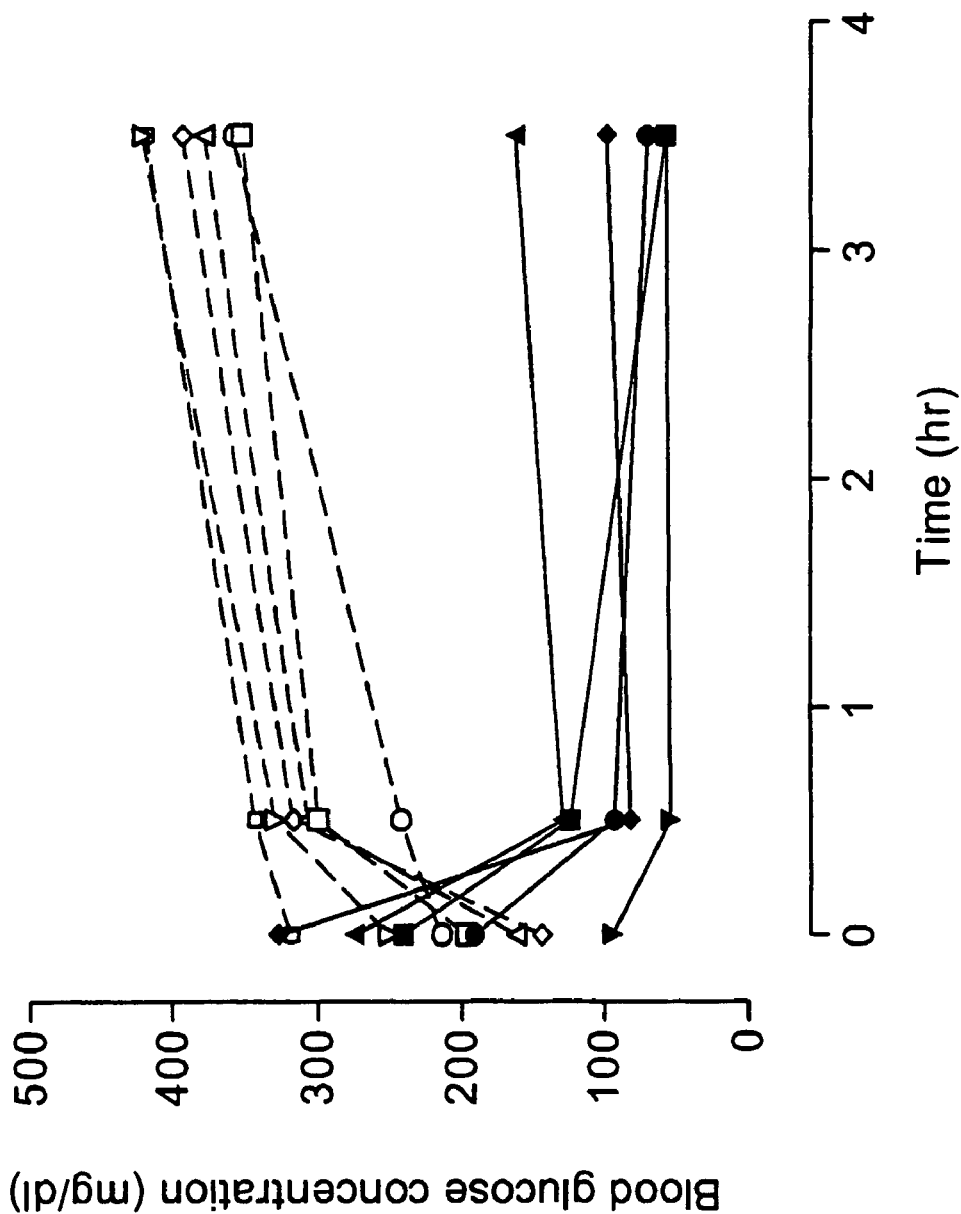

FIG. 12. Insulin administered orally does not diminish the blood glucose concentration of diabetic rats. In rats with stretopzotocin induced diabetes, parenterally administered insulin (Humulin, intermediate action, 6 IU) decreases the blood glucose concentration (continuous lines). Instead, when insulin (30 IU) is administered orally the concentration of glucose remains high (dashed lines).

Figure 13:
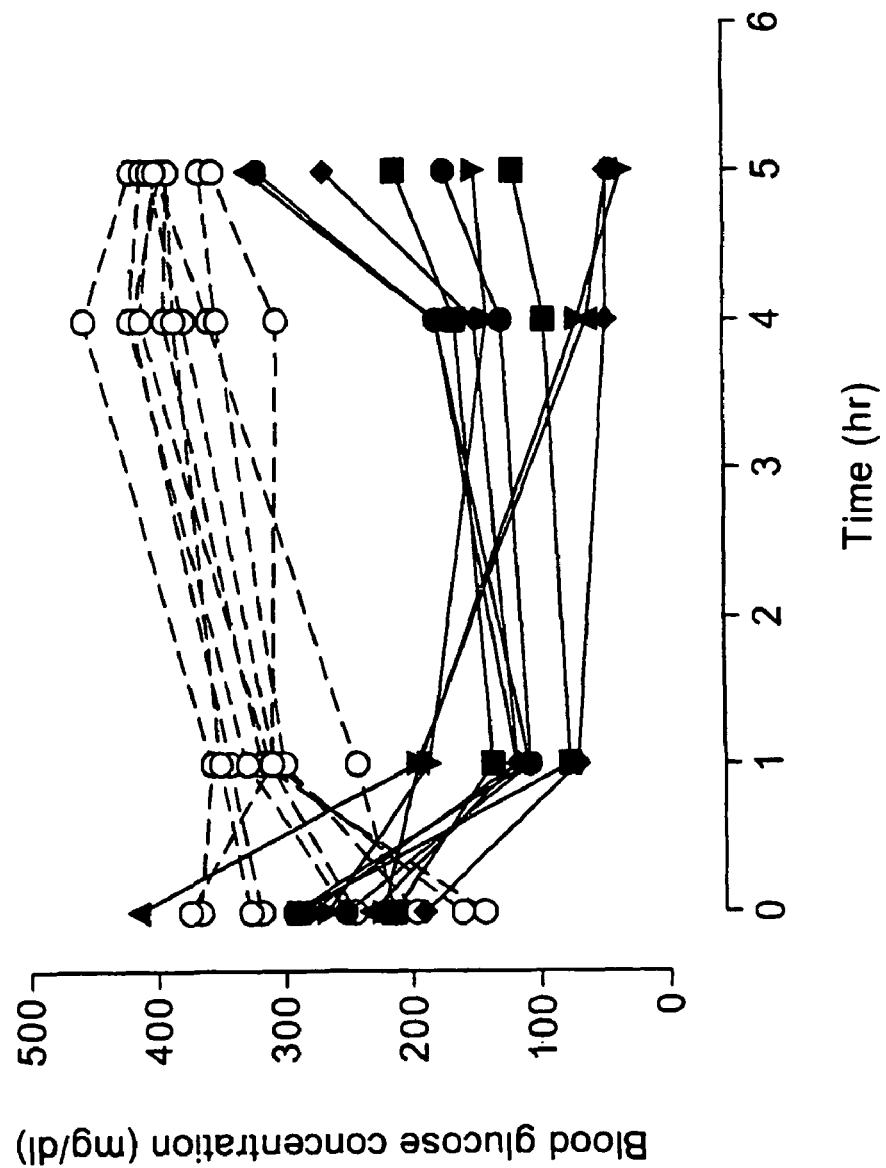

FIG. 13. When insulin is administered orally together with VP8, the blood glucose concentration diminishes. Rats with streptozotocin induced diabetes received orally VP8 (100 µg) (dashed lines) or VP8 (100 µg) and insulin (30 IU) (continuous lines). Only with the latter treatment the blood glucose concentration diminished.

DETAILED DESCRIPTION OF THE INVENTION

As noted above, the present invention deals with the use of rotavirus protein VP4 (SEQ. ID No. 1) and its functional variants, as well as the derived proteins VP8 (SEQ: ID. No. 2) and VP8$_{141-182}$ (SEQ. ID. No. 3) and peptides derived from them (SEQ. ID. No. 4, 5, 6 and 7), to facilitate and/or enhance passage of pharmaceutical agents through epithelia and endothelia.

VP4 is a rotavirus protein. The particular strain of rotavirus from which VP4 is derived is not critical to the present invention.

The present invention considers any VP4 strain, independent of its origin, either natural or as a result of genetic manipulation, a functional variant of VP4, as long as it maintains the capacity to modulate the sealing of tight junctions.

Proteins VP4, VP8 or their derived fragments can be obtained and purified, e.g., by genetically engineered E. coli strains overexpressing their cDNA alone or fused to other genes, such as histidine or glutathione-s-transferase).

Proteins VP4, VPB, and VP8$_{141-182}$ can be employed to generate antibodies, either monoclonals or polyclonals, that can be used to generate the same effect on tight junctions as proteins VP4, VP8 or their derived fragments and peptides, by employing methods well known in the art (Abrams et al., 1986).

Alternatively, proteins VP4 and VP8 can be employed either in their full length, in shorter versions, as fusion proteins or as derived synthetic functional peptides.

In yet another aspect of the invention, methods are proposed to determine the regions of protein VP4 that facilitate or enhance the opening of TJ. Such methods employ the following procedures:

A) Extraction and/or culture of an epithelia or endothelia.

B) Determination of the transepithelial electrical resistance of such epithelia/endothelia.

C) Determine if after the addition of peptides, fragments or fusion proteins derived from rotavirus protein VP4 to epithelia/endothelia, the transepithelial electrical resistance decreases.

D) Optionally, molecules or drugs that are incapable of traversing the paracellular pathway (e.g. mannitol, dextran) when TJ are closed, can be employed to determine if paracellular leakage is induced by peptides, fragments or fusion proteins derived from rotavirus protein VP4.

As employed in the present invention, a "decrease in transepithelial electrical resistance" means a decrease in the resistance offered by the TJ to the passage of ions and molecules through the paracellular pathway.

The assay to determine the biological activity of proteins VP4, VP8 or their derived fragments and peptides, is not critical to the present invention. For example, the assay may involve (1) assaying for a decrease of tissue resistance of ileum mounted in Ussing chambers (Fasano et al., 1991) (2) assaying for a decrease of tissue resistance of epithelia cell line monolayers in Ussing chambers as described in Example 1 below; or (3) assaying for intestinal or nasal enhancement of absorption of a therapeutic agent, as described in U.S. Pat. No. 5,827,534 and U.S. Pat. No. 5,665,389.

Within another aspect of the invention, proteins VP4, VP8 or their derived fragments and peptides, could be employed for treating cancers, such as pancreatic cancer, where epithelial transformation is related to over expression of tight junction proteins (e.g. claudin-4) (Michl et al., 2001).

Furthermore, proteins VP4, VP8 or their derived fragments and peptides, could be employed to treat cancer and/or inhibit metastasis, by disrupting the TJ of new capillaries, whose formation constitute a prerequisite for tumor growth and the emergence of metastases.

Within another related aspect protein VP4, its derived polypeptide VP8, or peptides derived from them can be used to reduce unwanted cellular adhesion that can occur between normal cells as a result of surgery, injury, chemotherapy, disease, inflammation or other condition jeopardizing cell viability or function.

Proteins VP4 and VP8 can be obtained and purified by methods known to the art, for example by the methods referred to in example 1.

As employed in the present invention "functional peptide" or "functional protein" refers to any polypeptide derived from VP4 that is capable of decreasing the transepithelial electrical resistance and/or is able to modulate the structure of TJ, and/or the appearance of its molecular components.

In another aspect of the invention pharmaceutical compositions are described for the delivery of a therapeutic compound, where such compositions comprise:

A) a therapeutic agent, and

B) An enhancing effective amount of proteins VP4, VP8 or their derived fragments and peptides.

The pharmaceutical composition is preferably an oral dosage composition for intestinal delivery, a nasal dosage composition for nasal delivery or intravenous dosage composition for delivery of a therapeutic agent through the blood-brain barrier.

The oral dosage composition for intestinal delivery comprises:

C) a therapeutic agent, and

D) An enhancing effective amount of proteins VP4, VP8 or their derived fragments and peptides, that allows the absorption of the therapeutic agent through the intestinal epithelium.

Oral dosage compositions for ileum delivery are well known in the art. Such oral dosage compositions can be in the form of solutions, tablets or capsules.

In the context of the present invention, oral dosage compositions include liquid compositions that contain aqueous agents. In such compositions it is recommended that the composition be prepared just before its administration, in order to minimise potential problems with the stability of the proteins and polypeptides of this invention.

The nasal dosage composition for nasal delivery of a therapeutic agent comprises:

A) a therapeutic agent; and

B) a nasal absorption enhancing effective amount of VP4, VP8 or their derived fragments and peptides.

Nasal dosage compositions for nasal delivery are well known in the art. Such nasal dosage compositions generally comprise water-soluble polymers that have been used extensively to prepare pharmaceutical dosage forms. The particular water-soluble polymer employed is not critical to the present invention, and can be selected from any of the well-known water-soluble polymers employed for nasal dosage forms.

The intravenous dosage composition for delivery of a therapeutic agent through the blood-brain barrier comprises:

(A) a therapeutic agent; and (B) a blood-brain barrier absorption enhancing effective amount of VP4, VP8 or their derived fragments and peptides.

Intravenous dosage compositions for delivery to the brain are well known in the art. Such intravenous dosage compositions generally comprise a physiological diluent, e.g., distilled water, or 0.9% (w/v) NaCl.

A "nasal" delivery composition differs from an "intestinal" delivery composition in that the latter must have gastroresistent properties in order to prevent the acidic degradation of the active agents (e.g. VP4, VP8 or their derived fragments and peptides and the therapeutic agent) in the stomach, whereas the former generally comprises water-soluble polymers in order to reduce the mucociliary clearance, and to achieve a reproducible bioavailability of the nasally administered agents. An "intravenous" delivery composition differs from both the "nasal" and "intestinal" delivery compositions in that there is no need for gastroresistance or water-soluble polymers in the "intravenous" delivery composition.

The mode of administration is not critical to the present invention. Although, it is preferable that the mode of administration is orally, for the intestinal delivery composition; intranasally, for the nasal delivery composition; and intravenously for delivery through the blood-brain barrier.

The particular therapeutic agent employed is not critical to the present invention, and can be, e.g., any drug compound, biologically active peptide, vaccine, or any other moiety otherwise not absorbed through the transcellular pathway, regardless of size or charge.

Examples of drug compounds, which can be employed in the present invention, include drugs that act on the cardiovascular system, drugs that act on the central nervous system, antineoplastic drugs and antibiotics.

Examples of drugs that act on the cardiovascular system, which can be employed in the present invention, include lidocaine, adenosine, dobutamine, dopamine, epinephrine, norepinephrine and phentolamine.

Examples of drugs that act on the central nervous system, which can be employed in the present invention, include doxapram, alfentanil, dezocin, nalbuphine, buprenorphine, naloxone, ketorolac, midazolam, propofol, metacurine, mivacurium and succinylcholine.

Examples of antineoplastic drugs that can be employed in the present include cytarabine, mitomycin, doxorubicin, vincristine and vinblastine.

Examples of antibiotics that can be employed in the present include methicillin, mezlocillin, piperacillin, cetoxitin, cefonicid, cefmetazole and aztreonam.

Examples of biologically active peptides that can be employed in the present invention include hormones, lymphokines, globulins, and albumins.

Examples of hormones which can be employed in the present invention include testosterone, nandrolene, menotropins, progesterone, insulin and urofolltropin.

Examples of lymphokines that can be employed in the present invention include interferon-alpha, interferon-beta, interferon-gamma, interleukin-1, interleukin-2, interleukin-4 and interleukin-8.

Examples of globulins that can be employed in the present invention include alpha-globulins, beta-globulins and gamma.-globulins (immunoglobulin).

Examples of immunoglobulins which can be employed in the present invention include polyvalent IgG or specific IgG, IgA and IgM, e.g., anti-tetanus antibodies.

An example of albumin that can be employed in the present invention is human serum albumin and ovalbumin.

Examples of vaccines that can be employed in the present invention include peptide antigens and attenuated micro-organisms and viruses.

Examples of peptide antigens which can be employed in the present invention include the B subunit of the heat-labile enterotoxin of enterotoxigenic *E. coli*, the B subunit of cholera toxin, capsular antigens of enteric pathogens, fimbriae or pili of enteric pathogens, HIV surface antigens, dust allergens and acari allergens.

Examples of attenuated micro-organisms and viruses that can be employed in the present invention include those of enterotoxigenic *Escherichia coli*, enteropathogenic *Escherichia coli*, *Vibrio cholerae*, *Shigella flexneri*, *Salmonella typhi*, and *Helicobacter pylori*.

When the therapeutic agent is insulin, the pharmaceutical composition of the present invention is useful for the treatment of diabetes.

The amount of therapeutic agent employed is not critical to the present invention and will vary depending upon the particular agent selected, the disease or condition being treated, as well as the age, weight and sex of the subject being treated.

The amount of VP4, VP8 or their derived fragments and peptides employed is also not critical to the present invention and will vary depending upon the age, weight and sex of the subject being treated.

The ratio of therapeutic agent to of VP4, VP8 or their derived fragments and peptides employed is not critical to the present invention and will vary depending upon the amount of therapeutic agent to be delivered within the selected period of time.

The following examples are offered by way of illustration and not by way of limitation.

EXAMPLE 1

Effect of Rotavirus Protein VP8 on the Degree of Sealing of Epithelial Monolayers This example illustrates an assay for evaluating the effect of rotavirus proteins on transepithelial electrical resistance.

A) VP8 Cloning

The RRV VP8 fragment (VP4 gene nucleotides 1 to 750) was cloned in pGEX-4T-1 (Pharmacia) and in pET6HIS plasmids as previously described (Dowling et al., 2000; Isa et al., 1997).

B) VP5 Cloning

The RRV VP5 fragment (VP4 gene nucleotides 749 to 2347) was cloned in pGEX4T-2 (Pharmacia) as previously described (Zarate et al., 2000b).

C) Expression, Purification, and Administration of Fusion Proteins

Expression and purification of fusion proteins was performed following previously described standard procedures (Frangioni et al., 1993). For their experimental use, fusion proteins VP5 and VP8 were dissolved in fresh Dulbecco's minimal essential medium (DMEM) and sterilized by passage through a 0.22 μm filtration unit.

D) Cell Culture

MDCK cells were cultured as previously described (Gonzalez-Mariscal et al., 1990) and used for experiments between passages 70-90.

E) Transepithelial Electrical Resistance Measurements

The degree of sealing of tight junctions was evaluated by measuring the transepithelial electrical resistance (TER) across the monolayer. Standard procedures were followed (Gonzalez-Mariscal et al., 1990). Briefly, monolayers grown over Millipore filters were mounted between two Lucite chambers with an exposed area of 0.23 cm2. Current was delivered via Ag—AgCl electrodes placed at 2.0 cm form the monolayer; the voltage deflection elicited was measured with a second set of electrodes placed at 1.0 mm from the membrane. The contribution if the filter and the bathing solution was subtracted, and all values reported correspond exclusively to the monolayer. Each disk was used for a single determination.

FIG. 1 shows how the addition of 4 μg/ml of VP8-GST or VP8-His, but not of 4 μg/ml of VP5-GST significantly reduces the TER of epithelial monolayers after 30 min. of treatment. Observe how the effect of VP8 upon the electrical resistance of the monolayer becomes reversible with time. To further illustrate the latter point we developed another assay in which GST-VPB was withdrawn from the culture media. In FIG. 2 observe how in these monolayers the TER of the monolayers is restored.

FIG. 3 shows how the effect of VP8 upon TER is dose dependent.

EXAMPLE 2

VP8 Modifies the Cell Border Distribution of TJ Proteins

This example illustrated an epithelial cell assay for evaluating the effect of VP8 on the distribution of TJ proteins.

A) Immunolocalization of TJ Proteins.

MDCK cells were cultured in glass coverslips. Confluent cultures were exposed to 4 μg/ml of GST-VP8 for 1 hr. The cells were then fixed for 30 min with 2% p-formaldehyde in PBS, pH 7.4, and permeabilized for 3 min with 0.2% PBS-TX. Cells were washed five times with PBS and then blocked for 30 minutes with 1% BSA Ig free (Research Organics 1331-a). The monolayers were incubated overnight at 4° C. with rabbit polyclonal antibodies against ZO-1 (Zymed 61-7300, dilution 1:100), Claudin 3 (Zymed 34-1700, dilution 3 μgr/ml) or occludin (Zymed 71-1500, dilution 1:100 in 1% Ig-free BSA). After being washed five times with PBS, the coverslips were incubated for one hour at room temperature with a secondary antibody (FITC-conjugated goat anti-rabbit, catalogue no. 65-6111, diluted 1:100, Zymed). The monolayers were washed five times in PBS before being mounted with the antifade reagent Vectashield (Vector Laboratories Inc.). The fluorescence of the monolayers was examined using a confocal microscope (MRC600, Bio-Rad) with a Krypton-argon laser.

FIG. 4. shows conspicuous sharp ring like structures of ZO-1, claudin-3 and occludin on the lateral membranes between neighbouring cells in control monolayers (arrowheads). In the control condition claudin-3 also gives a diffuse staining in the cytoplasm. In GST-VP8 treated monolayers, ZO-1 displays strong immuno reactivity in the cytoplasm (arrow). The honeycomb-like organization of claudin-3 is now altered by the appearance of large areas almost devoid of lateral staining (arrow) and occludin labeled monolayers show a broad and diffuse stain at the cell periphery (arrow). These results confirm that VP8 has altered the distribution of these TJ components.

EXAMPLE 3

Effect of VP8 on the Freeze Fracture Appearance of TJ

This example illustrates how the pattern of TJ filaments is modified by VP8.

A) Freeze Fracture Analysis of TJ.

Confluent monolayers of MDCK cells were incubated for 1 hour with 4 μg/ml of GST-VP8 dissolved in DMEM, while control monolayers remained in DMEM. Freeze-fracture replicas were obtained from monolayers fixed with 2.5% glutaraldehyde for 30 minutes, and gradually infiltrated with glycerol up to a 20% concentration, in which they were left for 1 hour. The monolayers were then detached from the substrate and frozen in liquid nitrogen. Freeze fracture was carried out at $-120°$ C., and $2 \times 10^{-6}$ mm Hg using a Balzers apparatus (BAF400T). After evaporation of platinum and carbon, the organic material was digested for 1 hour in chromic mixture. Replicas were extensively washed in distilled water and mounted in Formvar coated grids. The observations were done in an electron microscope JEOL 200EX.

To assess modifications in the pattern of TJ strands, we counted the number of strands intercepting lines drawn perpendicular to the main axis of the junction, every 48 nm, as well as the distance between the upper and lowermost strand. 59 and 54 μm of TJ networks were analysed respectively for control and VP8 treated monolayers.

As has been previously reported (Gonzalez-Mariscal et al., 1985) the amount of junction is defined by the following function:

$$\text{Amount of } TJ = \sum_{n=1}^{x} n_i \%_i$$

Where $n_i$ is the number of strands in a segment of TJ, and % is the percentage in which that number of strands is present in the sample.

Total junctional width is defined as:

$$\text{Total junctional width} = \sum_{n=1}^{x} n_i \%_i$$

Where $n_i$ is the distance between the upper and lowermost filament in TJ segment, and $\%_i$ is the percentage in which that width is present in the sample.

Figure 5A:
Figure 5B:
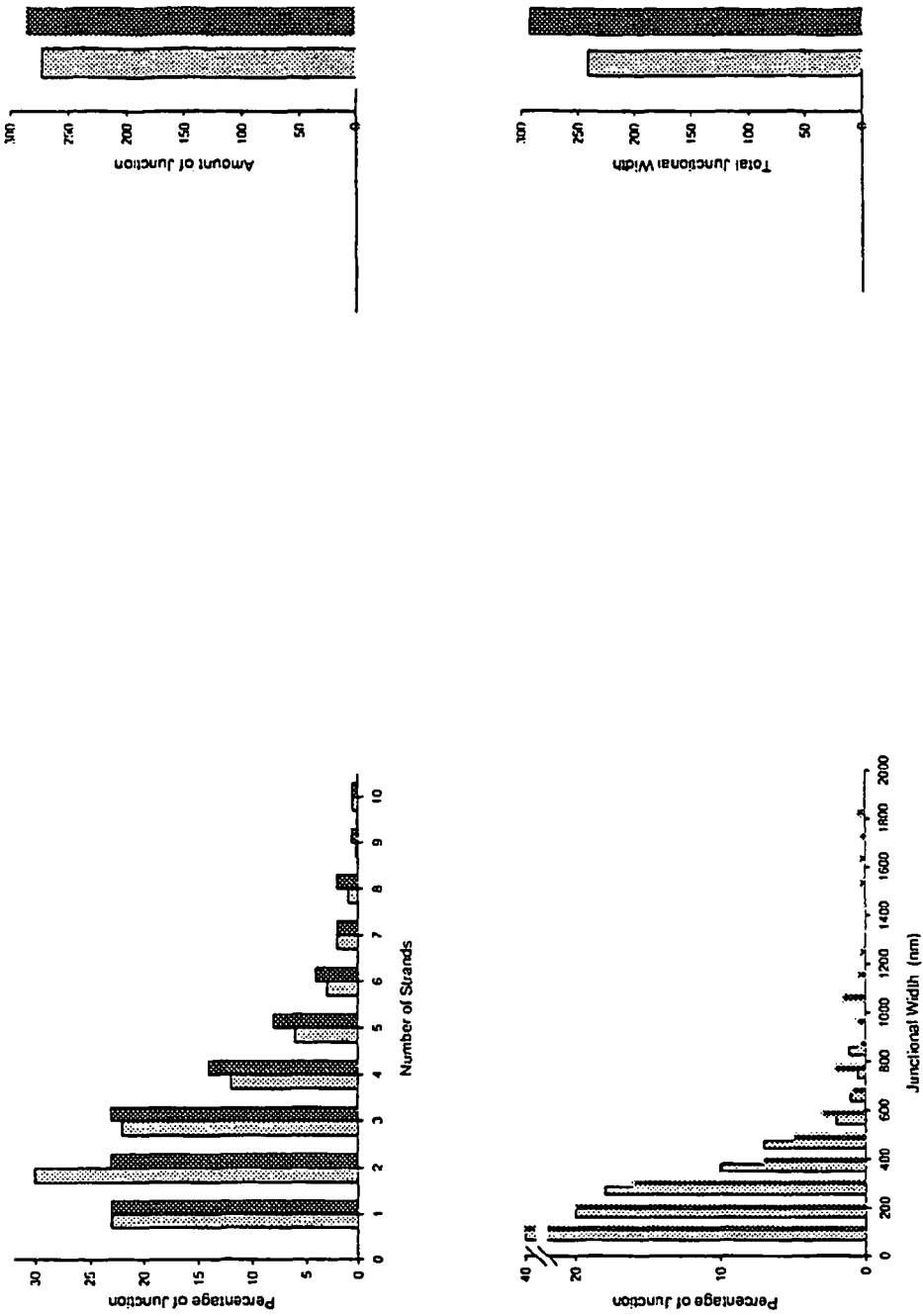

FIG. 5A shows a typical TJ freeze fracture pattern of MDCK cells. TJ are distinguished as a network of interconnecting fibrils in the P face of the plasma membrane complementary to grooves on the E face. Treatment with VP8 induces the appearance of loose ends oriented perpendicular to the network of TJ fibrils. The arrangement of the main TJ axis is also simpler, as filaments have lost their interconnected appearance. The image in FIG. 5B exemplifies the TJ pattern observed in VP8 treated monolayers.

The morphometric analysis present in the lower panel of FIG. 5, shows no change in the distribution of the number of TJ strands nor in the total amount of junction between control and VP8 treated monolayers. However, on analyzing the junctional width, it is clear that very profound junctions (950 to 1800 nm) appear in VP8 treated monolayers. This change is due to the frequent appearance in VP8 treated monolayers of loose ends that run perpendicular to the main junctional axis (Number of loose ends/linear amount of junction in μm=0.32 in VP8 treated monolayers Vs=0.17 in control monolayers). This change in the TJ pattern of VP8 treated cells, can explain the diminished TER observed in these monolayers.

EXAMPLE 4

Effect of VP8 on TJ Assembly

This example illustrates an epithelial assay for evaluating the effect of VP8 on the formation of TJ.

A) Calcium-Switch Assay for Evaluating TJ Assembly.

The ability of VP8 to inhibit the development of TJ was assessed utilizing the $Ca^{2+}$ switch assay (Gonzalez-Mariscal et al., 1990). Cells were plated at confluency on Millipore filters and incubated for 1 hour in DMEM (normal calcium media, NC; 1.8 mM $Ca^{2+}$). Then, the resulting monolayers were washed three times with PBS without $Ca^{2+}$ and transferred to minimal essential medium without $Ca^{2+}$ (low calcium media, LC; 1-5 μM $Ca^{2+}$). Twenty hours later experimental monolayers were transferred to LC media containing 4 μg/ml of GST-VP8 or of GST-VP5 dissolved in LC media, while control monolayers were again incubated in LC media. After 30 minutes, the experimental monolayers were transferred to NC media containing 4 μg/ml of GST-VP8 or of GST-VP5. Control monolayers received instead NC media. The TER was measured at different time points after the monolayers were transferred to NC media.

FIG. 6 shows how the addition of 4 μg/ml of GST-VP8 but not of GST-VP5 delays the development of the epithelial paracellular barrier in the calcium-switch assay.

EXAMPLE 5

Proteins and Peptides Derived from VP8 Modulate Tissue Permeability

This example illustrates a method for selecting domains of VP8 that can enhance or modulate the opening of TJ.

A) Identification of domains present in VP8 that resemble the extracellular loops of the TJ proteins occludin and claudins. We compared the amino acid sequence of rotavirus protein VP8 with that of the external loops of occludin and claudins 1 to 20. We observed that a ≧50% similarity is present in several segments. We illustrate this observation in the shadowed sequences present in FIG. 7A. Then we show how these sequences of VP8 are conserved in the extracellular loops of occludin derived from different species (FIG. 7B), and among different claudins (FIG. 7C).

B) Generation of His fusion protein $VP8_{141-182}$ from a VP8 region containing several domains similar to the extracellular loops of claudins and occludin. The VP8 region that comprises amino acids 141-182 (SEQ. ID. No. 3) was selected since it contains several domains similar to regions present in occludin and claudin. A histidine fusion protein was constructed employing the pET6HIS plasmid, and expression and purification was done following standard procedures (Dowling et al., 2000).

C) Synthesis of some of the peptides present in VP8 that bear a ≧50% similarity to the extracellular loops of claudins and occludin. The peptides with SEQ. ID. No. 4: $_{144}VVKT_{147}$, SEQ. ID. No. 5: $_{151}SYSQYGPL_{158}$, SEQ. ID. No. 6: $_{174}IYTY_{177}$, and SEQ. ID. No. 7: $_{183}NVTT_{186}$ were synthesized by the American Peptide Company, Inc. with a purity superior to 80% in their cyclic form by the addition of a cysteine residue on the amino and carboxyl to terminal ends of each peptide.

D) TER assay for evaluating the effect of fusion protein $VP8_{141-182}$ on tissue permeability. The determination of the TER across an epithelial monolayer was done as described in Example 1.

FIG. 8 shows how the addition of 4 µg/ml of $VP8_{141-182}$ (SEQ. ID. No. 3) significantly reduces the TER of MDCK monolayers.

FIG. 9 demonstrates how the addition of 4 µg/ml of $VP8_{141-182}$ (SEQ. ID. No. 3) inhibits the development of the epithelial paracellular barrier in a calcium-switch assay.

FIG. 10 illustrates how the addition of the peptide with SEQ. ID. No. 7: $_{183}NVTT_{186}$ significantly reduces the TER of MDCK monolayers. In contrast, the administration of peptides with SEQ. ID. No. 4: $_{144}VVKT_{147}$; 5: $_{151}SYSQYGPL_{158}$ and 6: $_{174}IYTY_{177}$ exert no effect on the monolayer electrical resistance.

EXAMPLE 6

Effect of VP8 on the Oral Administering of Insulin to Diabetic Rats

This Example illustrates an assay for evaluating the effect of VP8 on orally administered insulin.

A) Generation of Diabetic Rats.

Male Wistar rats (230-250 gr.) were maintained on Pico-Lab® Rodent Diet 20, sterilized by irradiation and water ad libitum, in the animal house (temperature 22 to 24° C., 50 to 55% humidity). Care and handling of the animals were in accordance to international recommended procedures.

Diabetes mellitus type I was induced with one intraperitoneal shot of streptozotocin (75 mg/Kg weight; Sigma, Cat. No. S0130), diluted in citrate buffer 0.1 M (Sigma, Cat. No. S4641) pH 4.5. Streptozotocin solution was prepared immediately before use and protected from light exposure.

B) Determination of Glucose Concentration in Blood.

Using heparinized capillary tubing (Chase Scientific Glass Inc. Cat. No. 2501) a drop of blood was taken from the eye orbital sinus of the rats. Blood glucose concentration was determined using reactive strips (One Touch, LIFESCAN, Johnson & Johnson) and a commercial glucometer (One Touch Basic Plus, LIFESCAN, Johnson & Johnson). Glucose concentration was determined in healthy animals and in those that had received the streptozotocin intraperitoneal shot at least three days before being tested.

FIG. 11 illustrates how the streptozotocin treatment significantly increased the level of glucose in the blood of the treated animals.

C) Administration of Insulin to Diabetic Rats.

In order to study the changes in glucose concentration generated by the administration of insulin, the first blood sample was taken from diabetic animals that had fasted overnight. Immediately after, the animals received their food (Lab Diet 5053), and 30 minutes later they were treated according to the following protocols: 1) Human insulin of intermediate action (3-6 IU/rat; Humulin® N, HI-310, Lilly) was parenterally administered. 2) Human insulin of intermediate action (15-30 IU/rat; Humulin® N, HI-310, Lilly) was given orally through an esophagic rat cannula (Fine Science Tools; Cat. No. 18061-75), in a solution of 400 µl of $NaHCO_3$ (1.5 g/100 ml, pH 8.3-8.4), to neutralize gastric acidity. 3) Employing an esophagic rat cannula, 100 µg of GST-VP8 and human insulin of intermediate action (15-30 IU/rat; Humulin® N, HI-310, Lilly) were administered orally in a solution of 400 µl $NaHCO_3$ (1.5 g/100 ml, pH 8.3-8.4). 4) 100 µg of GST-VP8 were administered orally through an esophagic rat cannula. The level of blood glucose was determined at different times after the start of each of the above described procedures.

FIG. 12 illustrates how insulin administered orally does not diminish the blood glucose concentration of diabetic rats, in contrast to insulin administered parenterally.

FIG. 13 shows how if insulin is administered orally together with VP8, the blood glucose concentration of diabetic rats diminishes significantly.

REFERENCE LIST

Abrams, P. G., Rossio, J. L., Stevenson, H. C., Foon, K. A., 1986. Optimal strategies for developing human-human monoclonal antibodies. Methods Enzymol. 121, 107-119.

Al Moustafa, A. E., Alaoui-Jamali, M. A., Batist, G., Hernandez-Perez, M., Serruya, C., Alpert, L., Black, M. J., Sladek, R., Foulkes, W. D., 2002. Identification of genes associated with head and neck carcinogenesis by cDNA microarray comparison between matched primary normal epithelial and squamous carcinoma cells. Oncogene. 21, 2634-2640.

Almeida, J. D., Hall, T., Banatvala, J. E., Totterdell, B. M., Chrystie, I. L., 1978. The effect of trypsin on the growth of rotavirus. J. Gen. Virol. 40, 213-218.

Avila-Flores, A., Rendon-Huerta, E., Moreno, J., Islas, S., Betanzos, A., Robles-Flores, M., Gonzalez-Mariscal, L., 2001. Tight-junction protein zonula occludens 2 is a target of phosphorylation by protein kinase C. Biochem. J. 360, 295-304.

Balda, M. S., Anderson, J. M., Matter, K., 1996a. The SH3 domain of the tight junction protein ZO-1 binds to a serine protein kinase that phosphorylates a region C-terminal to this domain. FEBS Lett. 399, 326-332.

Balda, M. S., Gonzalez-Mariscal, L., Contreras, R. G., Macias-Silva, M., Torres-Marquez, M. E., Garcia-Sainz, J.

A., Cereijido, M., 1991. Assembly and sealing of tight junctions: possible participation of G-proteins, phospholipase C, protein kinase C and calmodulin. J. Membr. Biol. 122, 193-202.

Balda, M. S. Matter, K., 2000. The tight junction protein ZO-1 and an interacting transcription factor regulate ErbB-2 expression. EMBO J. 19, 2024-2033.

Balda, M. S., Whitney, J. A., Flores, C., Gonzalez, S., Cereijido, M., Matter, K., 1996b. Functional dissociation of paracellular permeability and transepithelial electrical resistance and disruption of the apical-basolateral intramembrane diffusion barrier by expression of a mutant tight junction membrane protein. J. Cell Biol. 134, 1031-1049.

Bamforth, S. D., Kniesel, U., Wolburg, H., Engelhardt, B., Risau, W., 1999. A dominant mutant of occludin disrupts tight junction structure and function. J. Cell Sci. 112 (Pt 12), 1879-1888.

Blanchard, A., Jeunemaitre, X., Coudol, P., Dechaux, M., Froissart, M., May, A., Demontis, R., Fournier, A., Paillard, M., Houillier, P., 2001. Paracellin-1 is critical for magnesium and calcium reabsorption in the human thick ascending limb of Henle. Kidney Int. 59, 2206-2215.

Cereijido, M., Valdes, J., Shoshani, L., Contreras, R. G., 1998. Role of tight junctions in establishing and maintaining cell polarity. Annu. Rev. Physiol. 60, 161-177.

Citi, S., Sabanay, H., Jakes, R., Geiger, B., Kendrick-Jones, J., 1988. Cingulin, a new peripheral component of tight junctions. Nature. 333, 272-276.

Claude, P., 1978. Morphological factors influencing transepithelial permeability: a model for the resistance of the zonula occludens. J. Membr. Biol. 39, 219-232.

Coulson, B. S., Londrigan, S. L., Lee, D. J., 1997. Rotavirus contains integrin ligand sequences and a disintegrin-like domain that are implicated in virus entry into cells. Proc. Natl. Acad. Sci. U. S. A. 94, 5389-5394.

Dowling, W., Denisova, E., LaMonica, R., Mackow, E. R., 2000. Selective membrane permeabilization by the rotavirus VP5* protein is abrogated by mutations in an internal hydrophobic domain. J. Virol. 74, 6368-6376.

Enck, A. H., Berger, U. V., Yu, A. S., 2001. Claudin-2 is selectively expressed in proximal nephron in mouse kidney. Am. J. Physiol Renal Physiol. 281, F966-F974.

Espejo, R. T., Lopez, S., Arias, C., 1981. Structural polypeptides of simian rotavirus SA11 and the effect of trypsin. J. Virol. 37, 156-160.

Estes, M. K., 1996. Rotaviruses and their replication. In: Fields, B. N., Knipe, D. N., Howley, P. M., Chanock, R. M., Melnick, J. L., Monath, T. P., Roizman, B., and Straus, S. E. (Eds.), Fields Virology. New York, pp. 1625-1655.

Estes, M. K. Cohen, J., 1989. Rotavirus gene structure and function. Microbiol. Rev. 53, 410-449.

Fasano, A., 1999. Substancially pure zonulin, a physiological modulator of mammalian tight junctions. 859931, Fasano, A., Baudry, B., Pumplin, D. W., Wasserman, S. S., Tall, B. D., Ketley, J. M., Kaper, J. B., 1991. Vibrio cholerae produces a second enterotoxin, which affects intestinal tight junctions. Proc. Natl. Acad. Sci. U. S. A. 88, 5242-5246.

Fasano, A., Fiorentini, C., Donelli, G., Uzzau, S., Kaper, J. B., Margaretten, K., Ding, X., Guandalini, S., Comstock, L., Goldblum, S. E., 1995. Zonula occludens toxin modulates tight junctions through protein kinase C-dependent actin reorganization, in vitro. J. Clin. Invest. 96, 710-720.

Fiore, L., Greenberg, H. B., Mackow, E. R., 1991. The VP8 fragment of VP4 is the rhesus rotavirus hemagglutinin. Virology. 181, 553-563.

Frangioni, J. V. Neel, B. G., 1993. Solubilization and purification of enzymatically active glutathione S-transferase (PGEX) fusion proteins. Anal. Biochem. 210, 179-187.

Fukudome, K., Yoshie, O., Konno, T., 1989. Comparison of human, simian, and bovine rotaviruses for requirement of sialic acid in hemagglutination and cell adsorption. Virology. 172, 196-205.

Furuse, M., Furuse, K., Sasaki, H., Tsukita, S., 2001. Conversion of zonulae occludentes from tight to leaky strand type by introducing claudin-2 into Madin-Darby canine kidney I cells. J. Cell Biol. 153, 263-272.

Furuse, M., Hata, M., Furuse, K., Yoshida, Y., Haratake, A., Sugitani, Y., Noda, T., Kubo, A., Tsukita, S., 2002. Claudin-based tight junctions are crucial for the mammalian epidermal barrier: a lesson from claudin-1-deficient mice. J. Cell Biol. 156, 1099-1111.

Furuse, M., Hirase, T., Itoh, M., Nagafuchi, A., Yonemura, S., Tsukita, S., Tsukita, S., 1993. Occludin: a novel integral membrane protein localizing at tight junctions. J. Cell Biol. 123, 1777-1788.

Furuse, M., Sasaki, H., Tsukita, S., 1999. Manner of interaction of heterogeneous claudin species within and between tight junction strands. J. Cell Biol. 147, 891-903.

Gonzalez-Mariscal, L., Avila-Flores, A., Betanzos, A., 2001. The relationship between structure and function of tight junctions. In: Cereijido, M., Anderson, J. M. (Eds.), Tight Junctions. Boca Raton, pp. 89-119.

Gonzalez-Mariscal, L., Betanzos, A., Avila-Flores, A., 2000. MAGUK proteins: structure and role in the tight junction. Semin. Cell Dev. Biol. 11, 315-324.

Gonzalez-Mariscal, L., Chavez, D. R., Cereijido, M., 1985. Tight junction formation in cultured epithelial cells (MDCK). J. Membr. Biol. 86, 113-125.

Gonzalez-Mariscal, L., Contreras, R. G., Bolivar, J. J., Ponce, A., Chavez, D. R., Cereijido, M., 1990. Role of calcium in tight junction formation between epithelial cells. Am. J. Physiol. 259, C978-C986.

Goodenough, D. A. Wong, V., 1999. Paracellular channels! Science. 285, 62.

Guerrero, C. A., Mendez, E., Zarate, S., Isa, P., Lopez, S., Arias, C. F., 2000. Integrin alpha(v)beta(3) mediates rotavirus cell entry. Proc. Natl. Acad. Sci. U. S. A. 97, 14644-14649.

Hamazaki, Y., Itoh, M., Sasaki, H., Furuse, M., Tsukita, S., 2002. Multi-PDZ domain protein 1 (MUPP1) is concentrated at tight junctions through its possible interaction with claudin-1 and junctional adhesion molecule. J. Biol. Chem. 277, 455-461.

Hecht, G., 2002. Microbial Pathogens that affect tight junctions. In: Cereijido, M., Anderson, J. M. (Eds.), Tight Junctions. Boca Raton, pp. 493-515.

Hellani, A., Ji, J., Mauduit, C., Deschildre, C., Tabone, E., Benahmed, M., 2000. Developmental and hormonal regulation of the expression of oligodendrocyte-specific protein/claudin 11 in mouse testis. Endocrinology. 141, 3012-3019.

Hewish, M. J., Takada, Y., Coulson, B. S., 2000. Integrins alpha2beta1 and alpha4beta1 can mediate SA11 rotavirus attachment and entry into cells. J. Virol. 74, 228-236.

Hoevel, T., Macek, R., Mundigl, O., Swisshelm, K., Kubbies, M., 2002. Expression and targeting of the tight junction protein CLDN1 in CLDN1—negative human breast tumor cells. J. Cell Physiol. 191, 60-68.

Huber, D., Balda, M. S., Matter, K., 2000. Occludin modulates transepithelial migration of neutrophils. J. Biol. Chem. 275, 5773-5778.

Isa, P., Lopez, S., Segovia, L., Arias, C. F., 1997. Functional and structural analysis of the sialic acid-binding domain of rotaviruses. J. Virol. 71, 6749-6756.

Izumi, Y., Hirose, T., Tamai, Y., Hirai, S., Nagashima, Y., Fujimoto, T., Tabuse, Y., Kemphues, K. J., Ohno, S., 1998. An atypical PKC directly associates and colocalizes at the epithelial tight junction with ASIP, a mammalian homologue of Caenorhabditis elegans polarity protein PAR-3. J. Cell Biol. 143, 95-106.

Kachar, B. Reese, T. S., 1982. Evidence for the lipidic nature of tight junction strands. Nature. 296, 464-466.

Kapikian, A. Z. Chanock, R. M., 1996. Rotaviruses. In: Fields, B. N., Knipe, D. N., Howley, P. M., Chanock, R. M., Melnick, J. L., Monath, T. P., Roizman, B., and Straus, S. E. (Eds.), Virology. New York, pp. 1657-1708.

Kawabe, H., Nakanishi, H., Asada, M., Fukuhara, A., Morimoto, K., Takeuchi, M., Takai, Y., 2001. Pilt, a novel peripheral membrane protein at tight junctions in epithelial cells. J. Biol. Chem. 276, 48350-48355.

Keon, B. H., Schafer, S., Kuhn, C., Grund, C., Franke, W. W., 1996. Symplekin, a novel type of tight junction plaque protein. J. Cell Biol. 134, 1003-1018.

Kiuchi-Saishin, Y., Gotoh, S., Furuse, M., Takasuga, A., Tano, Y., Tsukita, S., 2002. Differential expression patterns of claudins, tight junction membrane proteins, in mouse nephron segments. J. Am. Soc. Nephrol. 13, 875-886.

Kojima, S., Rahner, C., Peng, S., Rizzolo, L. J., 2002. Claudin 5 is transiently expressed during the development of the retinal pigment epithelium. J. Membr. Biol. 186, 81-88.

Kramer, F., White, K., Kubbies, M., Swisshelm, K., Weber, B. H., 2000. Genomic organization of claudin-1 and its assessment in hereditary and sporadic breast cancer. Hum. Genet. 107, 249-256.

Lacaz-Vieira, F., Jaeger, M. M., Farshori, P., Kachar, B., 1999. Small synthetic peptides homologous to segments of the first external loop of occludin impair tight junction resealing. J. Membr. Biol. 168, 289-297.

Martin-Padura, I., Lostaglio, S., Schneemann, M., Williams, L., Romano, M., Fruscella, P., Panzeri, C., Stoppacciaro, A., Ruco, L., Villa, A., Simmons, D., Dejana, E., 1998. Junctional adhesion molecule, a novel member of the immunoglobulin superfamily that distributes at intercellular junctions and modulates monocyte transmigration. J. Cell Biol. 142, 117-127.

Martinez-Palomo, A., Meza, I., Beaty, G., Cereijido, M., 1980. Experimental modulation of occluding junctions in a cultured transporting epithelium. J. Cell Biol. 87, 736-745.

McCarthy, K. M., Skare, I. B., Stankewich, M. C., Furuse, M., Tsukita, S., Rogers, R. A., Lynch, R. D., Schneeberger, E. E., 1996. Occludin is a functional component of the tight junction. J. Cell Sci. 109 (Pt 9), 2287-2298.

Medina, R., Rahner, C., Mitic, L. L., Anderson, J. M., Van Itallie, C. M., 2000. Occludin localization at the tight junction requires the second extracellular loop. J. Membr. Biol. 178, 235-247.

Michl, P., Buchholz, M., Rolke, M., Kunsch, S., Lohr, M., McClane, B., Tsukita, S., Leder, G., Adler, G., Gress, T. M., 2001. Claudin-4: a new target for pancreatic cancer treatment using *Clostridium perfringens* enterotoxin. Gastroenterology. 121, 678-684.

Mitic, L. Van Itallie, C. M., 2001. Occludin and claudins: transmembrane proteins of the tight junction. In: Cereijido, M., Anderson, J. M. (Eds.), Tight Junctions. Boca Raton, pp. 213-230.

Morita, K., Sasaki, H., Fujimoto, K., Furuse, M., Tsukita, S., 1999a. Claudin-11/OSP-based tight junctions of myelin sheaths in brain and Sertoli cells in testis. J. Cell Biol. 145, 579-588.

Morita, K., Sasaki, H., Furuse, M., Tsukita, S., 1999b. Endothelial claudin: claudin-5/TMVCF constitutes tight junction strands in endothelial cells. J. Cell Biol. 147, 185-194.

Nishimura, M., Kakizaki, M., Ono, Y., Morimoto, K., Takeuchi, M., Inoue, Y., Imai, T., Takai, Y., 2002. JEAP, a novel component of tight junctions in exocrine cells. J. Biol. Chem. 277, 5583-5587.

Palmeri, D., van Zante, A., Huang, C. C., Hemmerich, S., Rosen, S. D., 2000. Vascular endothelial junction-associated molecule, a novel member of the immunoglobulin superfamily, is localized to intercellular boundaries of endothelial cells. J. Biol. Chem. 275, 19139-19145.

Reyes, J. L., Lamas, M., Martin, D., Namorado, M. C., Islas, S., Luna, J., Tauc, M., Gonzalez-Mariscal, L., 2002. The renal segmental distribution of claudins changes with development. Kidney International. 62, Saitou, M., Ando-Akatsuka, Y., Itoh, M., Furuse, M., Inazawa, J., Fujimoto, K., Tsukita, S., 1997. Mammalian occludin in epithelial cells: its expression and subcellular distribution. Eur. J. Cell Biol. 73, 222-231.

Saitou, M., Fujimoto, K., Doi, Y., Itoh, M., Fujimoto, T., Furuse, M., Takano, H., Noda, T., Tsukita, S., 1998. Occludin-deficient embryonic stem cells can differentiate into polarized epithelial cells bearing tight junctions. J. Cell Biol. 141, 397-408.

Saitou, M., Furuse, M., Sasaki, H., Schulzke, J. D., Fromm, M., Takano, H., Noda, T., Tsukita, S., 2000. Complex phenotype of mice lacking occludin, a component of tight junction strands. Mol. Biol. Cell. 11, 4131-4142.

Sakakibara, A., Furuse, M., Saitou, M., Ando-Akatsuka, Y., Tsukita, S., 1997. Possible involvement of phosphorylation of occludin in tight junction formation. J. Cell Biol. 137, 1393-1401.

Simon, D. B., Lu, Y., Choate, K. A., Velazquez, H., Al Sabban, E., Praga, M., Casari, G., Bettinelli, A., Colussi, G., Rodriguez-Soriano, J., McCredie, D., Milford, D., Sanjad, S., Lifton, R. P., 1999. Paracellin-1, a renal tight junction protein required for paracellular Mg2+ resorption. Science. 285, 103-106.

Sonoda, N., Furuse, M., Sasaki, H., Yonemura, S., Katahira, J., Horiguchi, Y., Tsukita, S., 1999. *Clostridium perfringens* enterotoxin fragment removes specific claudins from tight junction strands: Evidence for direct involvement of claudins in tight junction barrier. J. Cell Biol. 147, 195-204.

Tsukita, S., Furuse, M., Itoh, M., 2001. Multifunctional strands in tight junctions. Nat. Rev. Mol. Cell Biol. 2, 285-293.

Turksen, K. Troy, T. C., 2001. Claudin-6: a novel tight junction molecule is developmentally regulated in mouse embryonic epithelium. Dev. Dyn. 222, 292-300.

Van Itallie, C., Rahner, C., Anderson, J. M., 2001. Regulated expression of claudin-4 decreases paracellular conductance through a selective decrease in sodium permeability. J. Clin. Invest. 107, 1319-1327.

Vietor, I., Bader, T., Paiha, K., Huber, L. A., 2001. Perturbation of the tight junction permeability barrier by occludin loop peptides activates beta-catenin/TCF/LEF-mediated transcription. EMBO Rep. 2, 306-312.

Wang, W., Uzzau, S., Goldblum, S. E., Fasano, A., 2000. Human zonulin, a potential modulator of intestinal tight junctions. J. Cell Sci. 113 Pt 24, 4435-4440.

Wu, Z., Nybom, P., Magnusson, K. E., 2000. Distinct effects of Vibrio cholerae haemagglutinin/protease on the structure and localization of the tight junction-associated proteins occludin and ZO-1. Cell Microbiol. 2, 11-17.

Yamamoto, T., Harada, N., Kano, K., Taya, S., Canaani, E., Matsuura, Y., Mizoguchi, A., Ide, C., Kaibuchi, K, 1997. The Ras target AF-6 interacts with ZO-1 and serves as a peripheral component of tight junctions in epithelial cells. J. Cell Biol. 139, 785-795.

Zahraoui, A., Joberty, G., Arpin, M., Fontaine, J. J., Hellio, R., Tavitian, A., Louvard, D., 1994. A small rab GTPase is distributed in cytoplasmic vesicles in non polarized cells but colocalizes with the tight junction marker ZO-1 in polarized epithelial cells. J. Cell Biol. 124, 101-115.

Zarate, S., Espinosa, R., Romero, P., Guerrero, C. A., Arias, C. F., Lopez, S., 2000a. Integrin alpha2beta1 mediates the cell attachment of the rotavirus neuraminidase-resistant variant nar3. Virology. 278, 50-54.

Zarate, S., Espinosa, R., Romero, P., Mendez, E., Arias, C. F., Lopez, S., 2000b. The VP5 domain of VP4 can mediate attachment of rotaviruses to cells. J. Virol. 74, 593-599.

Zhong, Y., Saitoh, T., Minase, T., Sawada, N., Enomoto, K., Mori, M., 1993. Monoclonal antibody 7H6 reacts with a novel tight junction-associated protein distinct from ZO-1, cingulin and ZO-2. J. Cell Biol. 120, 477-483.

What is claimed is:

1. A pharmaceutical composition comprising:
   (A) a therapeutic agent; and
   (B) a protein or peptide consisting of the amino acid sequence of SEQ ID NO: 2, SEQ ID NO: 3 or SEQ ID NO: 7.

2. The pharmaceutical composition of claim 1, wherein said composition is an oral dosage composition.

3. The pharmaceutical composition of claim 1, wherein said composition is a nasal dosage composition.

4. The pharmaceutical composition of claim 1, wherein said composition is a cutaneous dosage composition.

5. The pharmaceutical composition of claim 1, wherein said composition is a vaginal dosage composition.

6. The pharmaceutical composition of claim 1, wherein said composition is a rectal dosage composition.

7. The pharmaceutical composition of claim 1, wherein said composition is in the form of an aerosol dosage composition.

8. The pharmaceutical composition of claim 1, wherein said composition is an intravenous dosage composition.

9. The pharmaceutical composition of claim 1, wherein said therapeutic agent is a drug, a peptide with biological activity, or an immunogenic composition.

10. The pharmaceutical composition of claim 9, wherein said biologically active peptide is selected from the group consisting of a hormone, lymphokine, globulin and albumin.

11. The pharmaceutical composition of claim 10, wherein said hormone is selected from the group consisting of testosterone, nandrolene, menotropins, insulin and urofolltropin.

12. The pharmaceutical composition of claim 1, wherein said therapeutic agent is insulin.

13. The pharmaceutical composition of claim 1, further comprising an acceptable pharmaceutical vehicle.

\* \* \* \* \*

SEQUENCE LISTING

<160> NUMBER OF SEQ ID NOS: 100

<210> SEQ ID NO 1
<211> LENGTH: 776
<212> TYPE: PRT
<213> ORGANISM: Rhesus Monkey Rotavirus

<400> SEQUENCE: 1

```
Met Ala Ser Leu Ile Tyr Arg Gln Leu Leu Thr Asn Ser Tyr Thr Val
  1               5                  10                  15

Asp Leu Ser Asp Glu Ile Gln Glu Ile Gly Ser Thr Lys Thr Gln Asn
             20                  25                  30

Val Thr Ile Asn Leu Gly Pro Phe Ala Gln Thr Gly Tyr Ala Pro Val
         35                  40                  45

Asn Trp Gly Pro Gly Glu Thr Asn Asp Ser Thr Thr Val Glu Pro Val
 50                  55                  60

Leu Asp Gly Pro Tyr Gln Pro Thr Ser Phe Asn Pro Pro Val Asp Tyr
 65                  70                  75                  80

Trp Met Leu Leu Ala Pro Thr Ala Ala Gly Val Val Val Glu Gly Thr
                 85                  90                  95

Asn Asn Thr Asp Arg Trp Leu Ala Thr Ile Leu Val Glu Pro Asn Val
            100                 105                 110

Thr Ser Glu Thr Arg Ser Tyr Thr Leu Phe Gly Thr Gln Glu Gln Ile
        115                 120                 125

Thr Ile Ala Tyr Ala Ser Gln Thr Gln Trp Lys Phe Ile Asp Val Val
130                 135                 140

Lys Thr Thr Gln Asn Gly Ser Tyr Ser Gln Tyr Gly Pro Leu Gln Ser
145                 150                 155                 160

Thr Pro Lys Leu Tyr Ala Val Met Lys His Asn Gly Lys Ile Tyr Thr
                165                 170                 175

Tyr Asn Gly Glu Thr Pro Asn Val Thr Thr Lys Tyr Tyr Ser Thr Thr
            180                 185                 190

Asn Tyr Asp Ser Val Asn Met Thr Ala Phe Cys Asp Phe Tyr Ile Ile
        195                 200                 205

Pro Arg Glu Glu Glu Ser Thr Cys Thr Glu Tyr Ile Asn Asn Gly Leu
    210                 215                 220

Pro Pro Ile Gln Asn Thr Arg Asn Ile Val Pro Leu Ala Leu Ser Ala
225                 230                 235                 240

Arg Asn Ile Ile Ser His Arg Ala Gln Ala Asn Glu Asp Ile Val Val
                245                 250                 255

Ser Lys Thr Ser Leu Trp Lys Glu Met Gln Tyr Asn Arg Asp Ile Thr
            260                 265                 270
```

-continued

```
Ile Arg Phe Lys Phe Ala Ser Ser Ile Val Lys Ser Gly Gly Leu Gly
        275                 280                 285

Tyr Lys Trp Ser Glu Ile Ser Phe Lys Pro Ala Asn Tyr Gln Tyr Thr
290                 295                 300

Tyr Thr Arg Asp Gly Glu Asp Val Thr Ala His Thr Thr Cys Ser Val
305                 310                 315                 320

Asn Gly Met Asn Asp Phe Asn Phe Asn Gly Gly Ser Leu Pro Thr Asp
                325                 330                 335

Phe Ile Ile Ser Arg Tyr Glu Val Ile Lys Glu Asn Ser Tyr Val Tyr
                340                 345                 350

Val Asp Tyr Trp Asp Asp Ser Gln Ala Phe Arg Asn Met Val Tyr Val
                355                 360                 365

Arg Ser Leu Ala Ala Asn Leu Asn Ser Val Ile Cys Thr Gly Gly Asp
370                 375                 380

Tyr Ser Phe Ala Leu Pro Val Gly Gln Trp Pro Val Met Thr Gly Gly
385                 390                 395                 400

Ala Val Ser Leu His Ser Ala Gly Val Thr Leu Ser Thr Gln Phe Thr
                405                 410                 415

Asp Phe Val Ser Phe Asn Ser Leu Arg Phe Arg Phe Arg Leu Thr Val
                420                 425                 430

Glu Glu Pro Ser Phe Ser Ile Thr Arg Thr Arg Val Gly Gly Leu Tyr
                435                 440                 445

Gly Leu Pro Ala Ala Tyr Pro Asn Asn Gly Lys Glu Tyr Tyr Glu Val
450                 455                 460

Ala Gly Arg Leu Ser Leu Ile Ser Leu Val Pro Ser Asn Asp Asp Tyr
465                 470                 475                 480

Gln Thr Pro Ile Thr Asn Ser Val Thr Val Arg Gln Asp Leu Glu Arg
                485                 490                 495

Gln Leu Gly Glu Leu Arg Glu Glu Phe Asn Ala Leu Ser Gln Glu Ile
                500                 505                 510

Ala Met Ser Gln Leu Ile Tyr Leu Ala Leu Leu Pro Leu Asp Met Phe
                515                 520                 525

Ser Met Phe Ser Gly Ile Lys Ser Thr Ile Asp Ala Ala Lys Ser Met
530                 535                 540

Ala Thr Ser Val Met Lys Lys Phe Lys Lys Ser Gly Leu Ala Asn Ser
545                 550                 555                 560

Val Ser Thr Leu Thr Asp Ser Leu Ser Asp Ala Ala Ser Ser Ile Ser
                565                 570                 575

Arg Gly Ala Ser Ile Arg Ser Val Gly Ser Ser Ala Ser Ala Trp Thr
                580                 585                 590

Asp Val Ser Thr Gln Ile Thr Asp Val Ser Ser Val Ser Ser Ile
                595                 600                 605

Ser Thr Gln Thr Ser Thr Ile Ser Arg Arg Leu Arg Leu Lys Glu Met
610                 615                 620

Ala Thr Gln Thr Glu Gly Met Asn Phe Asp Asp Ile Ser Ala Ala Val
625                 630                 635                 640

Leu Lys Thr Lys Ile Asp Arg Ser Thr Gln Ile Ser Pro Asn Thr Leu
                645                 650                 655

Pro Asp Ile Val Thr Glu Ala Ser Glu Lys Phe Ile Pro Asn Arg Ala
                660                 665                 670

Tyr Arg Val Ile Asn Asn Asp Glu Val Phe Glu Ala Gly Thr Asp Gly
                675                 680                 685

Arg Tyr Phe Ala Tyr Arg Val Glu Thr Phe Asp Glu Ile Pro Phe Asp
690                 695                 700
```

```
Val Gln Lys Phe Ala Asp Leu Val Thr Asp Ser Pro Val Ile Ser Ala
705                 710                 715                 720

Ile Ile Asp Phe Lys Thr Leu Lys Asn Leu Asn Asp Asn Tyr Gly Ile
                725                 730                 735

Ser Arg Gln Gln Ala Phe Asn Leu Leu Arg Ser Asp Pro Arg Val Leu
            740                 745                 750

Arg Glu Phe Ile Asn Gln Asp Asn Pro Ile Ile Arg Asn Arg Ile Glu
        755                 760                 765

Gln Leu Ile Met Gln Cys Arg Leu
    770                 775

<210> SEQ ID NO 2
<211> LENGTH: 231
<212> TYPE: PRT
<213> ORGANISM: Rhesus Monkey Rotavirus

<400> SEQUENCE: 2

Met Ala Ser Leu Ile Tyr Arg Gln Leu Leu Thr Asn Ser Tyr Thr Val
1               5                   10                  15

Asp Leu Ser Asp Glu Ile Gln Glu Ile Gly Ser Thr Lys Thr Gln Asn
                20                  25                  30

Val Thr Ile Asn Leu Gly Pro Phe Ala Gln Thr Gly Tyr Ala Pro Val
            35                  40                  45

Asn Trp Gly Pro Gly Glu Thr Asn Asp Ser Thr Thr Val Glu Pro Val
        50                  55                  60

Leu Asp Gly Pro Tyr Gln Pro Thr Ser Phe Asn Pro Pro Val Asp Tyr
65                  70                  75                  80

Trp Met Leu Leu Ala Pro Thr Ala Ala Gly Val Val Val Glu Gly Thr
                85                  90                  95

Asn Asn Thr Asp Arg Trp Leu Ala Thr Ile Leu Val Glu Pro Asn Val
                100                 105                 110

Thr Ser Glu Thr Arg Ser Tyr Thr Leu Phe Gly Thr Gln Glu Gln Ile
            115                 120                 125

Thr Ile Ala Tyr Ala Ser Gln Thr Gln Trp Lys Phe Ile Asp Val Val
        130                 135                 140

Lys Thr Thr Gln Asn Gly Ser Tyr Ser Gln Tyr Gly Pro Leu Gln Ser
145                 150                 155                 160

Thr Pro Lys Leu Tyr Ala Val Met Lys His Asn Gly Lys Ile Tyr Thr
                165                 170                 175

Tyr Asn Gly Glu Thr Pro Asn Val Thr Thr Lys Tyr Tyr Ser Thr Thr
                180                 185                 190

Asn Tyr Asp Ser Val Asn Met Thr Ala Phe Cys Asp Phe Tyr Ile Ile
            195                 200                 205

Pro Arg Glu Glu Glu Ser Thr Cys Thr Glu Tyr Ile Asn Asn Gly Leu
        210                 215                 220

Pro Pro Ile Gln Asn Thr Arg
225                 230

<210> SEQ ID NO 3
<211> LENGTH: 42
<212> TYPE: PRT
<213> ORGANISM: Rhesus Monkey Rotavirus

<400> SEQUENCE: 3

Ile Asp Val Val Lys Thr Thr Gln Asn Gly Ser Tyr Ser Gln Tyr Gly
1               5                   10                  15
```

```
Pro Leu Gln Ser Thr Pro Lys Leu Tyr Ala Val Met Lys His Asn Gly
            20                  25                  30

Lys Ile Tyr Thr Tyr Asn Gly Glu Thr Pro
            35                  40

<210> SEQ ID NO 4
<211> LENGTH: 4
<212> TYPE: PRT
<213> ORGANISM: Rhesus Monkey Rotavirus

<400> SEQUENCE: 4

Val Val Lys Thr
 1

<210> SEQ ID NO 5
<211> LENGTH: 8
<212> TYPE: PRT
<213> ORGANISM: Rhesus Monkey Rotavirus

<400> SEQUENCE: 5

Ser Tyr Ser Gln Tyr Gly Pro Leu
 1               5

<210> SEQ ID NO 6
<211> LENGTH: 4
<212> TYPE: PRT
<213> ORGANISM: Rhesus Monkey Rotavirus

<400> SEQUENCE: 6

Ile Tyr Thr Tyr
 1

<210> SEQ ID NO 7
<211> LENGTH: 4
<212> TYPE: PRT
<213> ORGANISM: Rhesus Monkey Rotavirus

<400> SEQUENCE: 7

Asn Val Thr Thr
 1

<210> SEQ ID NO 8
<211> LENGTH: 9
<212> TYPE: PRT
<213> ORGANISM: Rhesus Monkey Rotavirus

<400> SEQUENCE: 8

Gly Ser Tyr Ser Gln Tyr Gly Pro Leu
 1               5

<210> SEQ ID NO 9
<211> LENGTH: 45
<212> TYPE: PRT
<213> ORGANISM: Canis lupus familiaris

<400> SEQUENCE: 9

Asp Arg Gly Tyr Gly Thr Gly Leu Met Gly Ser Ile Gly Tyr Pro
 1               5                  10                  15

Tyr Gly Ser Gly Phe Gly Ser Tyr Gly Thr Gly Tyr Gly Tyr Gly Phe
            20                  25                  30

Gly Tyr Gly Tyr Gly Tyr Gly Gly Tyr Thr Asp Pro Arg
            35                  40                  45

<210> SEQ ID NO 10
```

```
<211> LENGTH: 44
<212> TYPE: PRT
<213> ORGANISM: Mus musculus

<400> SEQUENCE: 10

Asp Arg Gly Tyr Gly Thr Gly Leu Phe Gly Gly Ser Leu Asn Tyr Pro
1               5                   10                  15

Tyr Ser Gly Phe Gly Tyr Gly Gly Tyr Gly Gly Tyr Gly Gly
            20                  25                  30

Tyr Gly Tyr Gly Tyr Gly Gly Tyr Thr Asp Pro Arg
        35                  40

<210> SEQ ID NO 11
<211> LENGTH: 46
<212> TYPE: PRT
<213> ORGANISM: Rattus norvegicus

<400> SEQUENCE: 11

Asp Arg Ala Tyr Gly Thr Gly Ile Phe Gly Gly Ser Met Asn Tyr Pro
1               5                   10                  15

Tyr Gly Ser Gly Phe Gly Ser Tyr Gly Gly Phe Gly Gly Tyr Gly
            20                  25                  30

Tyr Gly Tyr Gly Tyr Gly Tyr Gly Gly Tyr Thr Asp Pro Arg
        35                  40                  45

<210> SEQ ID NO 12
<211> LENGTH: 46
<212> TYPE: PRT
<213> ORGANISM: Homo sapiens

<400> SEQUENCE: 12

Asp Arg Gly Tyr Gly Thr Ser Leu Leu Gly Gly Ser Val Gly Tyr Pro
1               5                   10                  15

Tyr Gly Gly Ser Gly Phe Gly Ser Tyr Gly Ser Gly Tyr Gly Tyr Gly
            20                  25                  30

Tyr Gly Tyr Gly Tyr Gly Tyr Gly Gly Tyr Thr Asp Pro Arg
        35                  40                  45

<210> SEQ ID NO 13
<211> LENGTH: 44
<212> TYPE: PRT
<213> ORGANISM: Gallus gallus

<400> SEQUENCE: 13

Asp Tyr Gly Tyr Gly Leu Gly Gly Ala Tyr Gly Thr Gly Leu Gly Gly
1               5                   10                  15

Phe Tyr Gly Ser Asn Tyr Tyr Gly Ser Gly Leu Ser Tyr Ser Tyr Gly
            20                  25                  30

Tyr Gly Gly Tyr Tyr Gly Gly Val Asn Gln Arg Thr
        35                  40

<210> SEQ ID NO 14
<211> LENGTH: 38
<212> TYPE: PRT
<213> ORGANISM: Dipodomys simulans

<400> SEQUENCE: 14

Glu Tyr Tyr Gly Ser Gly Gly Leu Leu Gly Tyr Gly Gly Leu Gly
1               5                   10                  15

Ser Tyr Tyr Asn Gly Tyr Tyr Gly Gly Tyr Asn Gly Tyr Tyr Gly
            20                  25                  30
```

```
Gly Leu Thr Asn Pro Arg
        35

<210> SEQ ID NO 15
<211> LENGTH: 45
<212> TYPE: PRT
<213> ORGANISM: Canis lupus familiaris

<400> SEQUENCE: 15

Pro Thr Ala Gln Ala Ser Gly Ser Leu Tyr Ser Ser Gln Ile Tyr Ala
 1               5                  10                  15

Met Cys Asn Gln Phe Tyr Ala Ser Thr Ala Thr Gly Leu Tyr Met Asp
                20                  25                  30

Gln Tyr Leu Tyr His Tyr Cys Val Val Asp Pro Gln Glu
        35                  40                  45

<210> SEQ ID NO 16
<211> LENGTH: 45
<212> TYPE: PRT
<213> ORGANISM: Mus musculus

<400> SEQUENCE: 16

Pro Thr Ala Gln Ala Ser Gly Ser Met Tyr Gly Ser Gln Ile Tyr Met
 1               5                  10                  15

Ile Cys Asn Gln Phe Tyr Thr Pro Gly Gly Thr Gly Leu Tyr Val Asp
                20                  25                  30

Gln Tyr Leu Tyr His Tyr Cys Val Val Asp Pro Gln Glu
        35                  40                  45

<210> SEQ ID NO 17
<211> LENGTH: 45
<212> TYPE: PRT
<213> ORGANISM: Rattus norvegicus

<400> SEQUENCE: 17

Pro Thr Ala Gln Ala Ser Gly Ser Met Tyr Gly Ser Gln Ile Tyr Thr
 1               5                  10                  15

Ile Cys Ser Gln Phe Tyr Thr Pro Gly Gly Thr Gly Leu Tyr Val Asp
                20                  25                  30

Gln Tyr Leu Tyr His Tyr Cys Val Val Asp Pro Gln Glu
        35                  40                  45

<210> SEQ ID NO 18
<211> LENGTH: 45
<212> TYPE: PRT
<213> ORGANISM: Homo sapiens

<400> SEQUENCE: 18

Pro Thr Ala Gln Ser Ser Gly Ser Leu Tyr Gly Ser Gln Ile Tyr Ala
 1               5                  10                  15

Leu Cys Asn Gln Phe Tyr Thr Pro Ala Ala Thr Gly Leu Tyr Val Asp
                20                  25                  30

Gln Tyr Leu Tyr His Tyr Cys Val Val Asp Pro Gln Glu
        35                  40                  45

<210> SEQ ID NO 19
<211> LENGTH: 41
<212> TYPE: PRT
<213> ORGANISM: Gallus gallus

<400> SEQUENCE: 19

Pro Gln Ala Gln Met Ser Ser Gly Tyr Tyr Tyr Ser Pro Leu Leu Ala
```

```
                1               5                  10                  15
Met Cys Ser Gln Ala Tyr Gly Ser Thr Tyr Leu Asn Tyr Ile Tyr
                    20                  25                  30

His Tyr Cys Thr Val Asp Pro Gln Glu
            35                  40

<210> SEQ ID NO 20
<211> LENGTH: 47
<212> TYPE: PRT
<213> ORGANISM: Dipodomys simulans

<400> SEQUENCE: 20

Pro Arg Ala Gly Leu Gly Ala Ser Ser Gly Ser Leu Tyr Tyr Asn Gln
1               5                   10                  15

Met Leu Met Leu Cys Asn Gln Met Met Ser Pro Val Ala Gly Gly Ile
                20                  25                  30

Met Asn Gln Tyr Leu Tyr His Tyr Cys Met Val Asp Pro Gln Glu
            35                  40                  45

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Ile Tyr Arg Gln Leu Leu
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Leu Ser Asp Glu Ile Gln
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide

<400> SEQUENCE: 23

Ser Thr Lys Thr Gln
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Pro Phe Ala Gln Thr Gly Tyr
1               5

<210> SEQ ID NO 25
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 25

Tyr Ala Pro Val Asn
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Leu Asp Gly Pro Tyr Gln
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide

<400> SEQUENCE: 27

Tyr Gln Pro Thr
1

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Phe Asn Pro Pro Val
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide

<400> SEQUENCE: 29

Trp Met Leu Leu Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Ala Gly Val Val Val Glu Gly
1               5

<210> SEQ ID NO 31
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 31

Thr Ser Glu Thr Arg Ser Tyr Thr Leu Phe Gly
 1               5                  10

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

Thr Arg Ser Tyr Thr Leu
 1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33

Ser Gln Thr Gln Trp Lys
 1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Val Val Lys Thr Thr
 1               5

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Tyr Ser Gln Tyr
 1

<210> SEQ ID NO 36
<211> LENGTH: 4
<212> TYPE: PRT
<213> ORGANISM: Artificial Sequence
<220> FEATURE:
<223> OTHER INFORMATION: Synthetic peptide

<400> SEQUENCE: 36

Tyr Gly Pro Leu
 1

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 37

Pro Lys Leu Tyr
 1

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

His Asn Gly Lys Ile Tyr
 1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Lys Ile Tyr Thr Tyr
 1               5

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide

<400> SEQUENCE: 40

Asn Val Thr Thr
 1

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Lys Tyr Tyr Ser Thr
 1               5

<210> SEQ ID NO 42
<211> LENGTH: 4
<212> TYPE: PRT
<213> ORGANISM: Artificial Sequence
<220> FEATURE:
<223> OTHER INFORMATION: Synthetic peptide

<400> SEQUENCE: 42

Tyr Asp Ser Val
 1

<210> SEQ ID NO 43
<211> LENGTH: 4
<212> TYPE: PRT
<213> ORGANISM: Artificial Sequence
<220> FEATURE:
<223> OTHER INFORMATION: Synthetic peptide

<400> SEQUENCE: 43
```

```
Cys Asp Phe Tyr
1

<210> SEQ ID NO 44
<211> LENGTH: 4
<212> TYPE: PRT
<213> ORGANISM: Artificial Sequence
<220> FEATURE:
<223> OTHER INFORMATION: Synthetic peptide

<400> SEQUENCE: 44

Cys Thr Glu Tyr
1

<210> SEQ ID NO 45
<211> LENGTH: 4
<212> TYPE: PRT
<213> ORGANISM: Artificial Sequence
<220> FEATURE:
<223> OTHER INFORMATION: Synthetic peptide

<400> SEQUENCE: 45

Tyr Asp Pro Met
1

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Lys Ile Tyr Ser Tyr
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic peptide

<400> SEQUENCE: 47

Asn Ile Tyr Thr
1

<210> SEQ ID NO 48
<211> LENGTH: 4
<212> TYPE: PRT
<213> ORGANISM: Artificial Sequence
<220> FEATURE:
<223> OTHER INFORMATION: Synthetic peptide

<400> SEQUENCE: 48

Tyr Asp Ser Leu
1

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide

<400> SEQUENCE: 49

Ile Tyr Ser Thr Leu Leu
```

<210> SEQ ID NO 50
<211> LENGTH: 4
<212> TYPE: PRT
<213> ORGANISM: Artificial Sequence
<220> FEATURE:
<223> OTHER INFORMATION: Synthetic peptide

<400> SEQUENCE: 50

Tyr Ser Pro Leu
1

<210> SEQ ID NO 51
<211> LENGTH: 4
<212> TYPE: PRT
<213> ORGANISM: Artificial Sequence
<220> FEATURE:
<223> OTHER INFORMATION: Synthetic peptide

<400> SEQUENCE: 51

Tyr Asp Ser Met
1

<210> SEQ ID NO 52
<211> LENGTH: 4
<212> TYPE: PRT
<213> ORGANISM: Artificial Sequence
<220> FEATURE:
<223> OTHER INFORMATION: Synthetic peptide

<400> SEQUENCE: 52

Cys Asp Ile Tyr
1

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide

<400> SEQUENCE: 53

Arg Asp Phe Tyr
1

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Pro Glu Ala Gln
1

<210> SEQ ID NO 55
<211> LENGTH: 4
<212> TYPE: PRT
<213> ORGANISM: Artificial Sequence
<220> FEATURE:
<223> OTHER INFORMATION: Synthetic peptide

<400> SEQUENCE: 55

Tyr Asn Pro Val
1

```
<210> SEQ ID NO 56
<211> LENGTH: 5
<212> TYPE: PRT
<213> ORGANISM: Artificial Sequence
<220> FEATURE:
<223> OTHER INFORMATION: Synthetic peptide

<400> SEQUENCE: 56

Tyr Asn Pro Val Val
 1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide

<400> SEQUENCE: 57

Val Val Gln Ser Thr
 1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic peptide

<400> SEQUENCE: 58

Tyr Asp Ser Leu
 1

<210> SEQ ID NO 59
<211> LENGTH: 4
<212> TYPE: PRT
<213> ORGANISM: Artificial Sequence
<220> FEATURE:
<223> OTHER INFORMATION: Synthetic peptide

<400> SEQUENCE: 59

Tyr Asn Pro Met
 1

<210> SEQ ID NO 60
<211> LENGTH: 5
<212> TYPE: PRT
<213> ORGANISM: Artificial Sequence
<220> FEATURE:
<223> OTHER INFORMATION: Synthetic peptide

<400> SEQUENCE: 60

Tyr Asn Pro Met Val
 1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic peptide

<400> SEQUENCE: 61

Val Val Gln Ser Thr
 1               5

<210> SEQ ID NO 62
```

```
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Tyr Asp Ser Leu
 1

<210> SEQ ID NO 63
<211> LENGTH: 4
<212> TYPE: PRT
<213> ORGANISM: Artificial Sequence
<220> FEATURE:
<223> OTHER INFORMATION: Synthetic peptide

<400> SEQUENCE: 63

Arg Asp Phe Tyr
 1

<210> SEQ ID NO 64
<211> LENGTH: 6
<212> TYPE: PRT
<213> ORGANISM: Artificial Sequence
<220> FEATURE:
<223> OTHER INFORMATION: Synthetic peptide

<400> SEQUENCE: 64

Leu Ser Ala Glu Val Gln
 1               5

<210> SEQ ID NO 65
<211> LENGTH: 4
<212> TYPE: PRT
<213> ORGANISM: Artificial Sequence
<220> FEATURE:
<223> OTHER INFORMATION: Synthetic peptide

<400> SEQUENCE: 65

Tyr Asp Pro Thr
 1

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide

<400> SEQUENCE: 66

Ala Gln Thr Thr Trp Lys
 1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide

<400> SEQUENCE: 67

Tyr Asn Pro Leu Val
 1               5

<210> SEQ ID NO 68
<211> LENGTH: 4
<212> TYPE: PRT
```

-continued

```
<213> ORGANISM: Artificial Sequence
<220> FEATURE:
<223> OTHER INFORMATION: Synthetic peptide

<400> SEQUENCE: 68

Tyr Asn Pro Leu
1

<210> SEQ ID NO 69
<211> LENGTH: 4
<212> TYPE: PRT
<213> ORGANISM: Artificial Sequence
<220> FEATURE:
<223> OTHER INFORMATION: Synthetic peptide

<400> SEQUENCE: 69

Tyr Asp Ser Leu
1

<210> SEQ ID NO 70
<211> LENGTH: 5
<212> TYPE: PRT
<213> ORGANISM: Artificial Sequence
<220> FEATURE:
<223> OTHER INFORMATION: Synthetic peptide

<400> SEQUENCE: 70

Tyr Asn Pro Leu Val
1               5

<210> SEQ ID NO 71
<211> LENGTH: 4
<212> TYPE: PRT
<213> ORGANISM: Artificial Sequence
<220> FEATURE:
<223> OTHER INFORMATION: Synthetic peptide

<400> SEQUENCE: 71

Tyr Asn Pro Leu
1

<210> SEQ ID NO 72
<211> LENGTH: 4
<212> TYPE: PRT
<213> ORGANISM: Artificial Sequence
<220> FEATURE:
<223> OTHER INFORMATION: Synthetic peptide

<400> SEQUENCE: 72

Tyr Asp Ser Ile
1

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide

<400> SEQUENCE: 73

Tyr Asn Pro Leu Val
1               5

<210> SEQ ID NO 74
<211> LENGTH: 4
<212> TYPE: PRT
<213> ORGANISM: Artificial Sequence
<220> FEATURE:
```

<223> OTHER INFORMATION: Synthetic peptide

<400> SEQUENCE: 74

Tyr Asn Pro Leu
1

<210> SEQ ID NO 75
<211> LENGTH: 4
<212> TYPE: PRT
<213> ORGANISM: Artificial Sequence
<220> FEATURE:
<223> OTHER INFORMATION: Synthetic peptide

<400> SEQUENCE: 75

Tyr Asp Ser Leu
1

<210> SEQ ID NO 76
<211> LENGTH: 4
<212> TYPE: PRT
<213> ORGANISM: Artificial Sequence
<220> FEATURE:
<223> OTHER INFORMATION: Synthetic peptide

<400> SEQUENCE: 76

Arg Asp Phe Tyr
1

<210> SEQ ID NO 77
<211> LENGTH: 5
<212> TYPE: PRT
<213> ORGANISM: Artificial Sequence
<220> FEATURE:
<223> OTHER INFORMATION: Synthetic peptide

<400> SEQUENCE: 77

Tyr Asn Pro Leu Val
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Ala Gln Val Val Trp Glu Val
1               5

<210> SEQ ID NO 79
<211> LENGTH: 4
<212> TYPE: PRT
<213> ORGANISM: Artificial Sequence
<220> FEATURE:
<223> OTHER INFORMATION: Synthetic peptide

<400> SEQUENCE: 79

Tyr Asn Pro Leu
1

<210> SEQ ID NO 80
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 80

Ile Asp Ser Val
1

<210> SEQ ID NO 81
<211> LENGTH: 4
<212> TYPE: PRT
<213> ORGANISM: Artificial Sequence
<220> FEATURE:
<223> OTHER INFORMATION: Synthetic peptide

<400> SEQUENCE: 81

Gln Asp Phe Tyr
1

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide

<400> SEQUENCE: 82

Leu Asp Gly Tyr Ile Gln
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic peptide

<400> SEQUENCE: 83

Thr Cys Ser Tyr Thr Ile
1               5

<210> SEQ ID NO 84
<211> LENGTH: 4
<212> TYPE: PRT
<213> ORGANISM: Artificial Sequence
<220> FEATURE:
<223> OTHER INFORMATION: Synthetic peptide

<400> SEQUENCE: 84

Tyr Ser Leu Tyr
1

<210> SEQ ID NO 85
<211> LENGTH: 4
<212> TYPE: PRT
<213> ORGANISM: Artificial Sequence
<220> FEATURE:
<223> OTHER INFORMATION: Synthetic peptide

<400> SEQUENCE: 85

Phe Glu Pro Val
1

<210> SEQ ID NO 86
<211> LENGTH: 5
<212> TYPE: PRT
<213> ORGANISM: Artificial Sequence
<220> FEATURE:
<223> OTHER INFORMATION: Synthetic peptide

<400> SEQUENCE: 86
```

```
Ser Lys Lys Val Gln
1               5

<210> SEQ ID NO 87
<211> LENGTH: 4
<212> TYPE: PRT
<213> ORGANISM: Artificial Sequence
<220> FEATURE:
<223> OTHER INFORMATION: Synthetic peptide

<400> SEQUENCE: 87

Cys Thr Leu Tyr
1

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide

<400> SEQUENCE: 88

Ile Tyr Arg Ser Leu Leu
1               5

<210> SEQ ID NO 89
<211> LENGTH: 5
<212> TYPE: PRT
<213> ORGANISM: Artificial Sequence
<220> FEATURE:
<223> OTHER INFORMATION: Synthetic peptide

<400> SEQUENCE: 89

Tyr Asn Pro Leu Val
1               5

<210> SEQ ID NO 90
<211> LENGTH: 4
<212> TYPE: PRT
<213> ORGANISM: Artificial Sequence
<220> FEATURE:
<223> OTHER INFORMATION: Synthetic peptide

<400> SEQUENCE: 90

Tyr Asn Pro Leu
1

<210> SEQ ID NO 91
<211> LENGTH: 4
<212> TYPE: PRT
<213> ORGANISM: Artificial Sequence
<220> FEATURE:
<223> OTHER INFORMATION: Synthetic peptide

<400> SEQUENCE: 91

Pro Leu Leu Pro
1

<210> SEQ ID NO 92
<211> LENGTH: 6
<212> TYPE: PRT
<213> ORGANISM: Artificial Sequence
<220> FEATURE:
<223> OTHER INFORMATION: Synthetic peptide

<400> SEQUENCE: 92

His Ser Thr Gly Ile Tyr
1               5
```

```
<210> SEQ ID NO 93
<211> LENGTH: 6
<212> TYPE: PRT
<213> ORGANISM: Artificial Sequence
<220> FEATURE:
<223> OTHER INFORMATION: Synthetic peptide

<400> SEQUENCE: 93

Leu Ala Leu Ser Gly Tyr
1               5

<210> SEQ ID NO 94
<211> LENGTH: 4
<212> TYPE: PRT
<213> ORGANISM: Artificial Sequence
<220> FEATURE:
<223> OTHER INFORMATION: Synthetic peptide

<400> SEQUENCE: 94

Pro Ala Leu Tyr
1

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide

<400> SEQUENCE: 95

Trp Met Val Asn Ala
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic peptide

<400> SEQUENCE: 96

Lys Phe Tyr Ser Ser
1               5

<210> SEQ ID NO 97
<211> LENGTH: 4
<212> TYPE: PRT
<213> ORGANISM: Artificial Sequence
<220> FEATURE:
<223> OTHER INFORMATION: Synthetic peptide

<400> SEQUENCE: 97

Cys Lys Phe Tyr
1

<210> SEQ ID NO 98
<211> LENGTH: 9
<212> TYPE: PRT
<213> ORGANISM: Artificial Sequence
<220> FEATURE:
<223> OTHER INFORMATION: Synthetic peptide

<400> SEQUENCE: 98

Thr Val Gln Thr Arg Tyr Thr Phe Gly
1               5
```

```
<210> SEQ ID NO 99
<211> LENGTH: 6
<212> TYPE: PRT
<213> ORGANISM: Artificial Sequence
<220> FEATURE:
<223> OTHER INFORMATION: Synthetic peptide

<400> SEQUENCE: 99

Leu Asp Gly His Ile Gln
 1               5

<210> SEQ ID NO 100
<211> LENGTH: 4
<212> TYPE: PRT
<213> ORGANISM: Artificial Sequence
<220> FEATURE:
<223> OTHER INFORMATION: Synthetic peptide

<400> SEQUENCE: 100

Cys Thr Trp Tyr
 1
```